(12) United States Patent
Ellis et al.

(10) Patent No.: US 10,376,518 B2
(45) Date of Patent: Aug. 13, 2019

(54) METHODS FOR THE TREATMENT OF AUTOIMMUNE DISEASES

(71) Applicant: UCL Business PLC, London (GB)

(72) Inventors: Shawn Ellis, London (GB); Clare Notley, London (GB); Michael Ehrenstein, London (GB)

(73) Assignee: UCL BUSINESS PLC, London (GB)

(*) Notice: Subject to any disclaimer, the term of this patent is extended or adjusted under 35 U.S.C. 154(b) by 300 days.

(21) Appl. No.: 14/780,104

(22) PCT Filed: Mar. 28, 2014

(86) PCT No.: PCT/GB2014/051005
§ 371 (c)(1),
(2) Date: Sep. 25, 2015

(87) PCT Pub. No.: WO2014/155135
PCT Pub. Date: Oct. 2, 2014

(65) Prior Publication Data
US 2016/0030439 A1 Feb. 4, 2016

(30) Foreign Application Priority Data
Mar. 28, 2013 (GB) .................. 1305714.6

(51) Int. Cl.
*A61K 39/395* (2006.01)
*A61K 31/5377* (2006.01)
*A61K 45/06* (2006.01)
*A61K 31/4155* (2006.01)
*C07K 16/28* (2006.01)
*G01N 33/564* (2006.01)
*G01N 33/68* (2006.01)

(52) U.S. Cl.
CPC ...... *A61K 31/5377* (2013.01); *A61K 31/4155* (2013.01); *A61K 39/3955* (2013.01); *A61K 39/39591* (2013.01); *A61K 45/06* (2013.01); *C07K 16/2809* (2013.01); *G01N 33/564* (2013.01); *G01N 33/6893* (2013.01); *C07K 2317/76* (2013.01); *G01N 2333/47* (2013.01); *G01N 2333/7051* (2013.01); *G01N 2800/102* (2013.01); *G01N 2800/105* (2013.01)

(58) Field of Classification Search
None
See application file for complete search history.

(56) References Cited

U.S. PATENT DOCUMENTS

2004/0097555 A1* 5/2004 Ohkawa ............. A61K 31/4439
514/342

FOREIGN PATENT DOCUMENTS

| WO | 2005/051293 A2 | 6/2005 |
| WO | 2008/009711 A2 | 1/2008 |
| WO | 2011/050106 A2 | 4/2011 |
| WO | 2011/127299 A1 | 10/2011 |

OTHER PUBLICATIONS

Mor et al., 2005. J. Immunol. vol. 175: 3439-3445.*
Golovina et al., 2008, J. Immunol. vol. 181: 2855-2868.*
Chevalier et al., 2013, Blood vol. 121: 29-37.*
Notley et al., 2010, Arth. Rheum. vol. 62: 171-178.*
Lourenco et al., 2009, J. Immunol. vol. 15: 182:7415-7421.*
Nabozny et al., 2002, Arthri. Rhem. vol. 44: S368.*
Pargellis et al. (2002) "Inhibition of p38 MAP kinase by utilizing a novel allosteric binding site," Nature Structural Biology. 9(4):268-272.
Regan et al. (2003) "Structure-activity relationships of the p38alpha MAP kinase inhibitor 1-(5-tert-butyl-2-p-tolyl-2H-pyrazol-3-yl)-3-[4-(2-morpholin-4-yl-ethoxy)naph-thalen-1-yl]urea (BIRB 796)," Journal of Medicinal Chemistry. 46(22):4676-4686.
Regan et al. (2003) "The kinetics of binding to p38MAP kinase by analogues of BIRB 796," Bioorganic and Medicinal Chemistry Letters. 13(18):3101-3104.
International Search Report with Written Opinion corresponding to International Search Report No. PCT/GB2014/051005, dated Jun. 24, 2014.
International Preliminary Report on Patentability corresponding to International Search Report No. PCT/GB2014/051005, dated Sep. 29, 2015.

* cited by examiner

*Primary Examiner* — Amy E Juedes
(74) *Attorney, Agent, or Firm* — Lathrop Gage LLP; Brian C. Trinque

(57) ABSTRACT

The present invention provides a method for inducing $CD8^+$ $FOXP3^+$ regulatory T cells in a subject which comprises administering to the subject: (i) a first agent which inhibits p38 phosphorylation; and (ii) a second agent which stimulates T-cell receptor (TCR) signalling. The method may be used to treat and/or prevent an autoimmune and/or inflammatory disease in a subject. The invention also provides compositions and kits for use in such methods.

11 Claims, 14 Drawing Sheets

|  | Untreated (n = 15) | Mtx (n = 28) | Ssz (n = 12) | Mtx+Ssz (n = 9) | Combined (n = 64) |
|---|---|---|---|---|---|
| Mean Age | 53 | 56 | 48 | 54 | 55 |
| (Range) | (34-79) | (23-92) | (40-83) | (25-82) | (23-92) |
| Mean CRP | 12.42 | 3.55 | 1.79 | 3.68 | 7.39 |
| (Range) | (1-84.9) | (1-18.3) | (0.6-11.7) | (0.7-20.4) | (0.6-84.9) |
| RF (+ve:-ve) | 8:7 | 18:10 | 10:2 | 8:1 | 43:21 |
| CCP (+ve:-ve) | 6:9 | 8:20 | 9:3 | 4:5 | 29:35 |

FIG. 9

METHODS FOR THE TREATMENT OF AUTOIMMUNE DISEASES

RELATED APPLICATIONS

This application is a 35 U.S.C. § 371 filing of International Application No. PCT/GB2014/051005, filed Mar. 28, 2014, which claims priority to Great Britain Patent Application No. 1305714.6, filed Mar. 28, 2013, each of which are incorporated herein by reference in their entireties.

FIELD OF THE INVENTION

The present invention relates to a method for inducing $CD8^+FOXP3^+$ regulatory T cells in a subject. The induction of $CD8^+FOXP3^+$ regulatory T cells is useful in the prevention and/or treatment of autoimmune and/or inflammatory conditions, such as rheumatoid arthritis. The present invention also relates to compositions and kits for use in such a method.

BACKGROUND TO THE INVENTION

Inflammation is involved in the pathogenesis of various diseases, encompassing autoimmunity, viral infections and cancer. A number of inflammatory autoimmune diseases are known, including psoriatic arthritis, diabetes and rheumatoid arthritis (RA). RA is characterized by systemic inflammation, accumulation of mononuclear cells in the synovium and impaired immunological tolerance.

Monoclonal antibodies (mAbs) targeting CD3 have been demonstrated to induce immune tolerance in some autoimmune diseases. Intact mAbs, although mitogenic, can establish long-term tolerance and stabilization of disease progression in patients recently diagnosed with type 1 diabetes mellitus (T1DM) and in the NOD and experimental autoimmune encephalomyelitis (EAE) mouse models of autoimmunity. The therapeutic effects of CD3-specific mAbs have been observed with the administration of modified antibodies or $F(Ab)_2$ fragments. The modified antibodies Teplizumab and Otelixizumab have been tested in T1 DM, these antibodies are not mitogenic and reduce the incidence and severity of cytokine release.

However, despite promising results from animal model and pre-clinical data, there has been limited success in using anti-CD3 therapy in humans. For example clinical trials using anti-CD3 therapy for RA have currently been stopped due to low efficacy. There have also been some problems in trials against diabetes, again due to inefficiency and dosage problems: http://clinicaltrials.gov/ct2/show/results/NCT00378508 http://www.genengnews.com/gen-news-high lights/macrogenics-and-lilly-ponder-future-of-diabetes-mab-after-phase-iii-flop/81244098/.

There is therefore a need for improved therapies for inflammatory and autoimmune diseases.

PBMC from RA patients were stained ex vivo and analyzed via flow cytometry. A live gate was defined on the forward scatter plotted against the side scatter. $CD8^+$ T cells were plotted against $CD4^+$ T cells to allow gating on $CD8^+$ T cells only. (A) Representative plots and cumulative data showing mean±SEM FOXP3 percentages gated on $CD8^+$ T cells from the whole PBMC of 17 healthy donors, 24 rheumatoid arthritis (RA) patients, 15 psoriatic arthritis (PsA) patients and 12 osteoarthritis (OA) patients. One-way repeated measures ANOVA used for statistical analysis. (B) FOXP3 was gated on the $CD8^+$ T cells. $CD8^+FOXP3^-$ ($FOXP3^-$) and $CD8^+FOXP3^+$ ($FOXP3^+$) T cells were then analyzed for expression of CD25 and TNFRII. Flow cytometry analysis of surface expression of TNFRII and CD25 by $CD8^+FOXP3^-$ and $CD8^+FOXP3^+$ T cells from RA PBMC. Tinted line represents the isotype control (iso), dotted line represents $CD8^+FOXP3^-$ T cells, black line represents $CD8^+FOXP3^+$ T cells. Cumulative data shows mean±SEM MFI of CD25 (n=4) and TNFRII (n=4) expressed on $CD8^+FOXP3^-$ and $CD8^+FOXP3^+$ T cells. Two-tailed t-test used for statistical analysis. (C) Representative flow cytometry plots displaying frequencies of IL-2, IFN-γ and IL-17 and FOXP3 by $CD8^+$ T cells from RA PBMC following 4 h stimulation with PMA and ionomycin (n=5).

Figure 2:
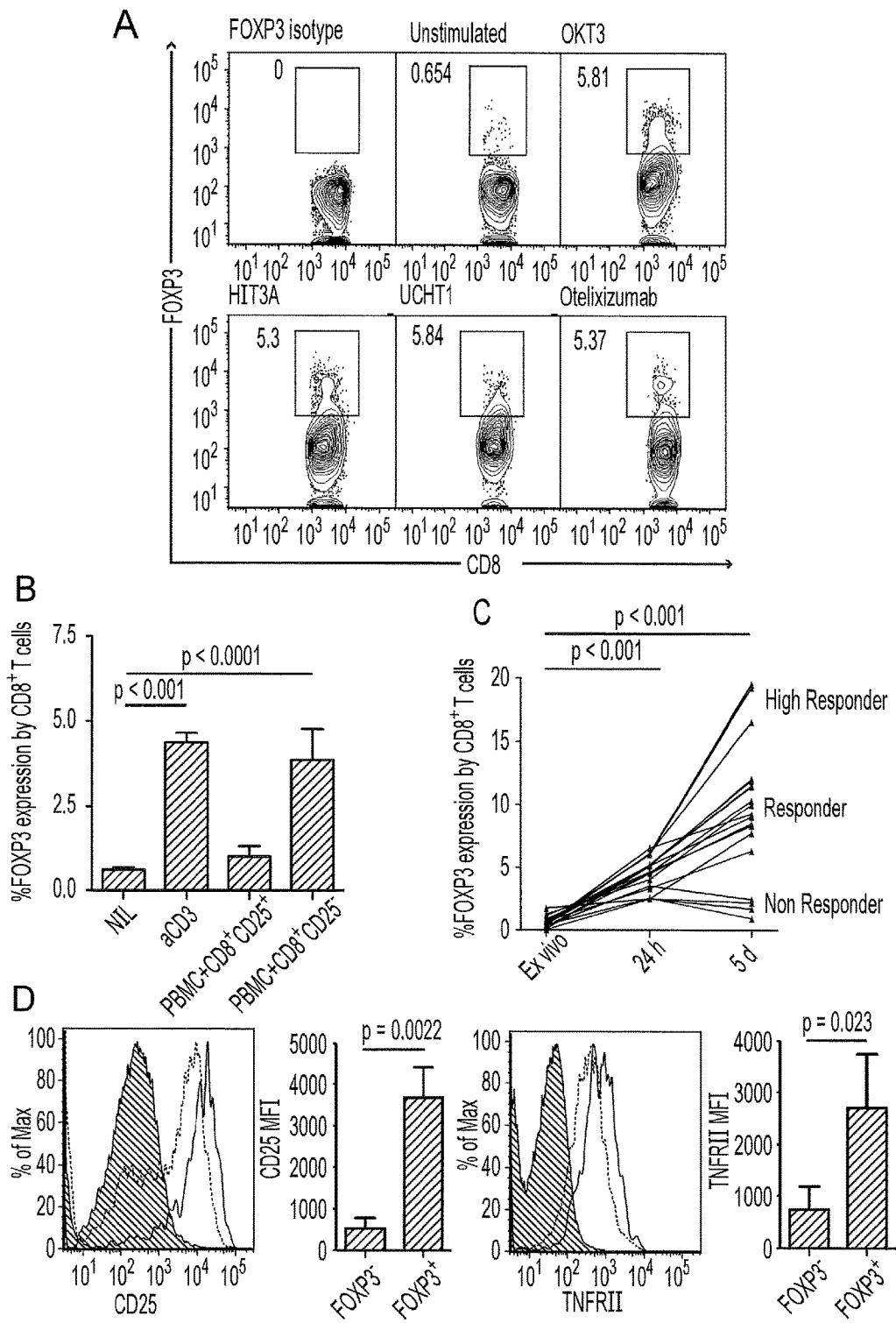

FIG. 2. Anti-CD3 mAb induces $CD8^+FOXP3^+$ Tregs from RA PBMC.

(A) Whole RA PBMC were unstimulated or cultured with 1 μg/ml OKT3, HIT3a, UCHT1 or Otelixizumab for 24 h. Samples were analyzed via flow cytometry. A live gate was defined on the forward scatter plotted against the side-scatter. $CD4^+$ T cells were plotted against $CD8^+$ T cells to allow analysis of $CD8^+$ T cells only for FOXP3 expression. An isotype control for FOXP3 was used to gate for $CD8^+FOXP3^+$ Treg. Numbers in plots indicate percentage of $CD8^+FOXP3^+$ Treg. (B) RA PBMC were depleted of $CD8^+$ T cells by magnetic bead sorting and the $CD8^+$ T cells divided into $CD8^+CD25^+$ T cells and $CD8^+CD25^-$ T cells. These cells were checked for their expression of FOXP3 ex vivo. These were reintroduced to PBMC depleted of $CD8^+$ T cells and cultured with OKT3 for 24 h and FOXP3 expression analyzed. Data shows mean±SEM of FOXP3 expression by $CD8^+$ T cells (n=4). One-way repeated measures ANOVA used for statistical analysis. (C) Cumulative and paired data of FOXP3 expression by $CD8^+$ T cells ex vivo, 24 h and 5 d after culture with OKT3 (n=18), paired t-test used for statistical analysis. (D) CD25 and TNFRII expression by $CD8^+FOXP3^+$ ($FOXP3^+$) and $CD8^+FOXP3^-$ ($FOXP3^-$) T cells after culture with OKT3 for 24 h. Tinted line represents the isotype control (iso), dotted line represents $CD8^+FOXP3^-$ T cells, black line represents $CD8^+FOXP3^+$ T cells. Cumulative data shows mean±SEM MFI of CD25 (n=4) and TNFRII (n=4). Two-tailed t-test used for statistical analysis.

Figure 3:
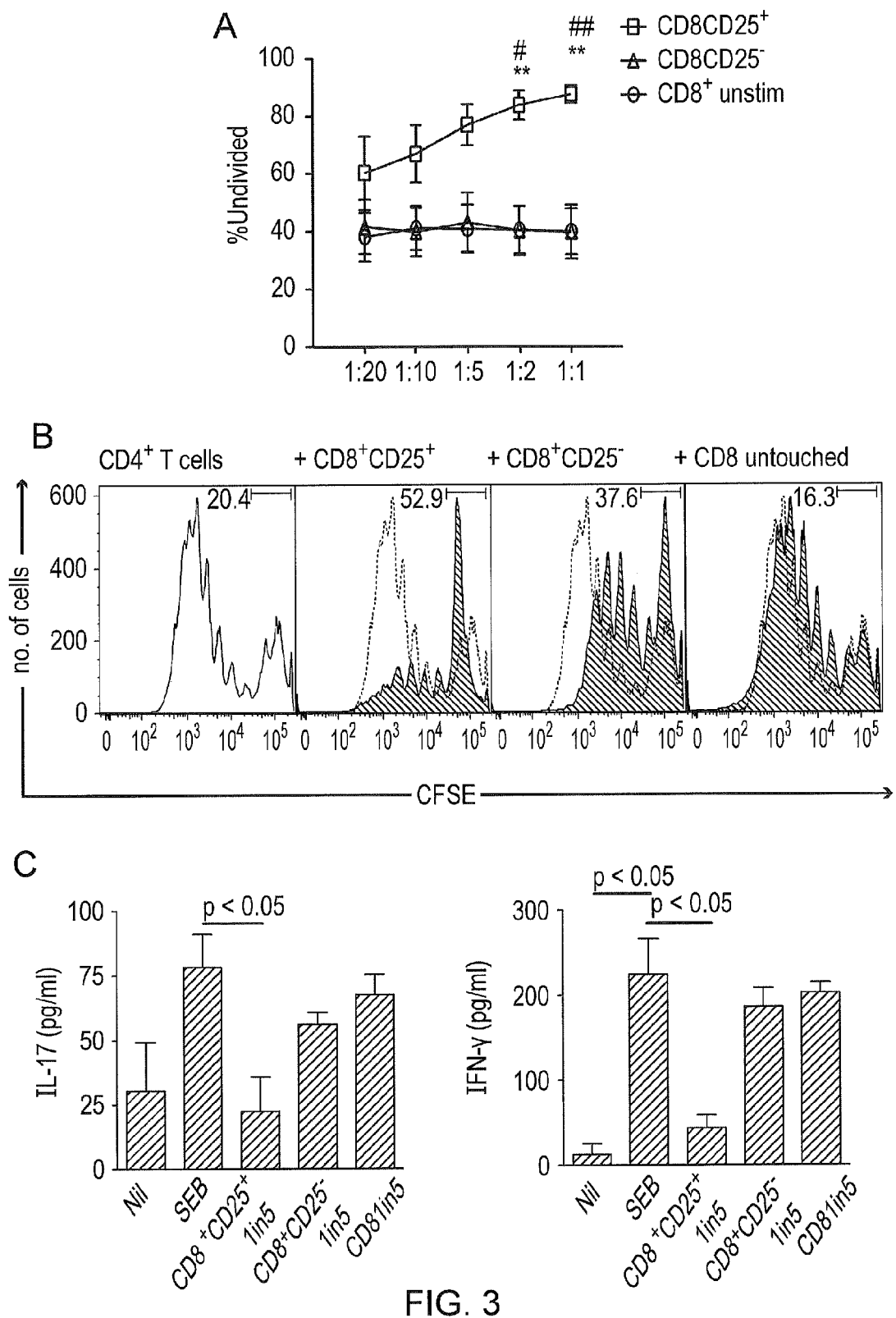

FIG. 3. $CD8^+CD25^+FOXP3^+$ Treg regulate $CD4^+$ T cell proliferation and cytokine production.

Whole RA PBMC were stimulated with 1 μg/ml OKT3 for 3 d, washed and rested for 2 d. $CD8^+$ T cells were isolated from cultures via bead sorting, then further divided into $CD8^+CD25^+$ and $CD8^+CD25^-$ T cells. CFSE labeled CD8 depleted PBMC were co-cultured with $CD8^+CD25^+$, $CD8^+CD25^-$ T cells or unstimulated $CD8^+$ T cells for 3 d or 5 d at ratios of 1 $CD8^+$ T cell to 1, 2, 5, 10 or 20 $CD4^+$ T cells, in the presence of 1 μg/ml staphylococcal enterotoxin B (SEB). (A and B) Proliferation by $CD4^+$ T cells was assessed by flow cytometry. % Undivided gate was determined by CFSE stained PBMC cultured in the absence of SEB. (A) Graph summarizing $CD4^+$ proliferation when cultured with $CD8^+CD25^+$ T cells ($CD8^+CD25^+$), $CD8^+CD25^-$ T cells ($CD8^+CD25^-$) or unstimulated $CD8^+$ T cells (CD8 unstim) for 3 d or (B) representative CFSE plots from 5 d cultures, #p<0.05, ###p<0.001 $CD8^+CD25^+$ versus $CD8^+$ unstimulated T cells at various ratios of $CD8^+$ T cells to $CD4^+$ T cells, **p<0.001 $CD8^+CD25^+$ versus $CD8^+CD25^-$ T cells, (n=6) One-way repeated measures ANOVA was used for statistical analysis. (c) Supernatants from 5 d cultures were analyzed by Mosaic ELISA for IL-17 and IFN-γ. Cumulative data showing mean±SEM of cytokine production (n=4). One-way repeated measures ANOVA was used for statistical analysis.

Figure 4:
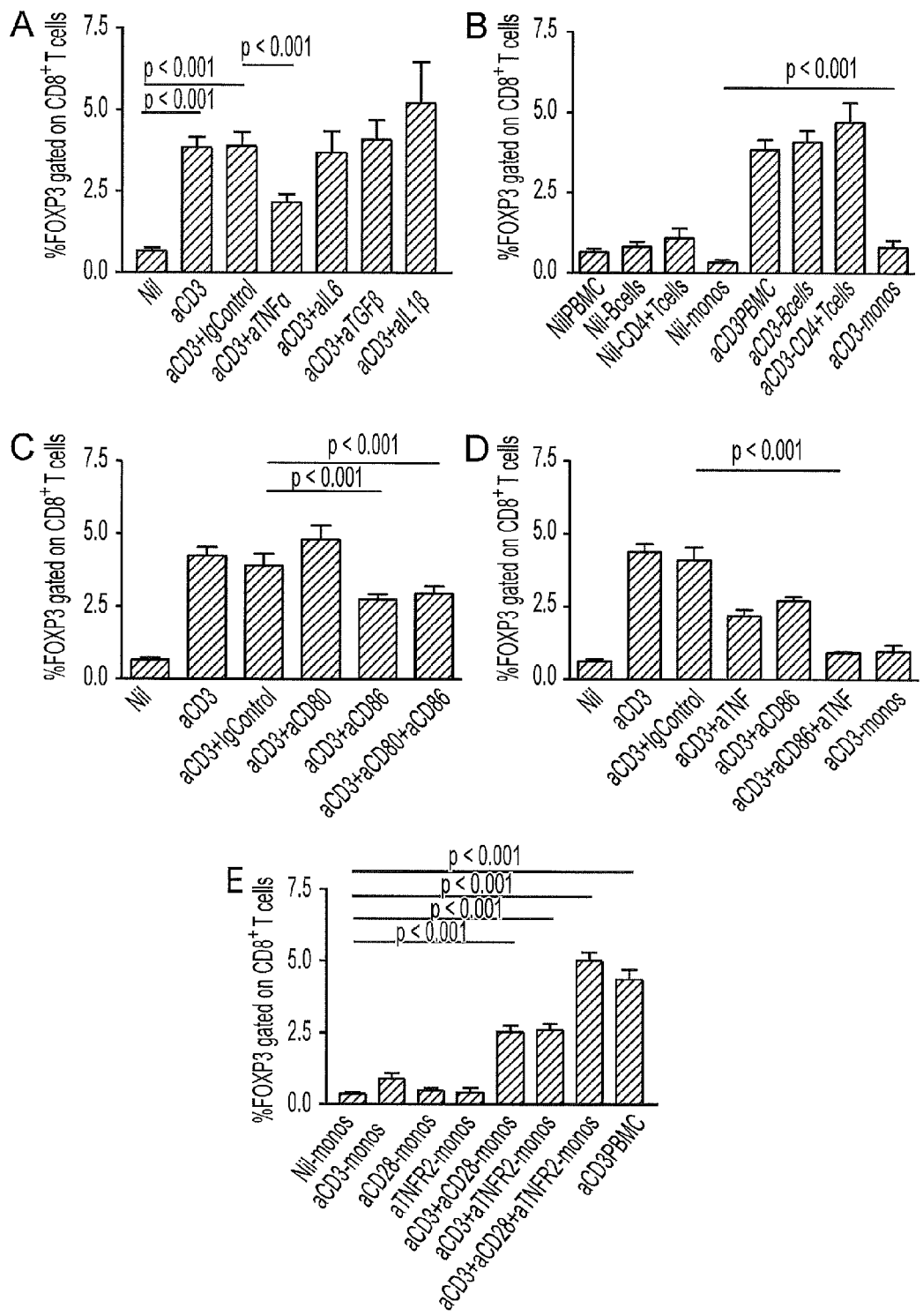

FIG. 4. Monocytes support CD8+FOXP3+ Treg induction by production of TNF-α.

Whole RA PBMC were either unstimulated or cultured with 1 µg/ml OKT3 for 24 h alone or in combination with an isotype control or (A) neutralizing antibodies to TNF-α (aTNFα) at 10 µg/ml, IL-6 (aIL6) at 0.1 µg/ml, TGF-β (TGFβ) at 12.5 µg/ml or IL-1β(IL1β) at 10 µg/ml. (B) Whole RA PBMC or PBMC depleted of B cells, CD4+ T cells or monocytes (monos) by magnetic bead sorting then unstimulated or cultured with 1 µg/ml OKT3 for 24 h. (c) Whole RA PBMC were either unstimulated or cultured with 1 µg/ml OKT3 for 24 h alone or in combination with an isotype control or (C) neutralizing antibodies to CD80 alone, CD86 alone or in combination, (D) TNF-α alone, CD86 alone or in combination. RA PBMC depleted of monocytes (-mono) and cultured with 1 µg/ml OKT for 24 h (E) RA PBMC depleted of monocytes (-mono) were either unstimulated or cultured with 1 µg/ml OKT3 or 1 µg/ml agonist antibodies to CD28 (aCD28) or TNFRII (aTNFRII) alone or in combination with one another for 24 h. RA PBMC were cultured with 1 µg/ml OKT3 for 24 h. All data were analyzed via flow cytometry for analysis of FOXP3 expression by CD8+ T cells. Graphs show cumulative data of the mean percentage±SEM of FOXP3 expression by CD8+ T cells (n=between 8 and 15). One-way repeated measures ANOVA was used for statistical analysis.

Figure 5:
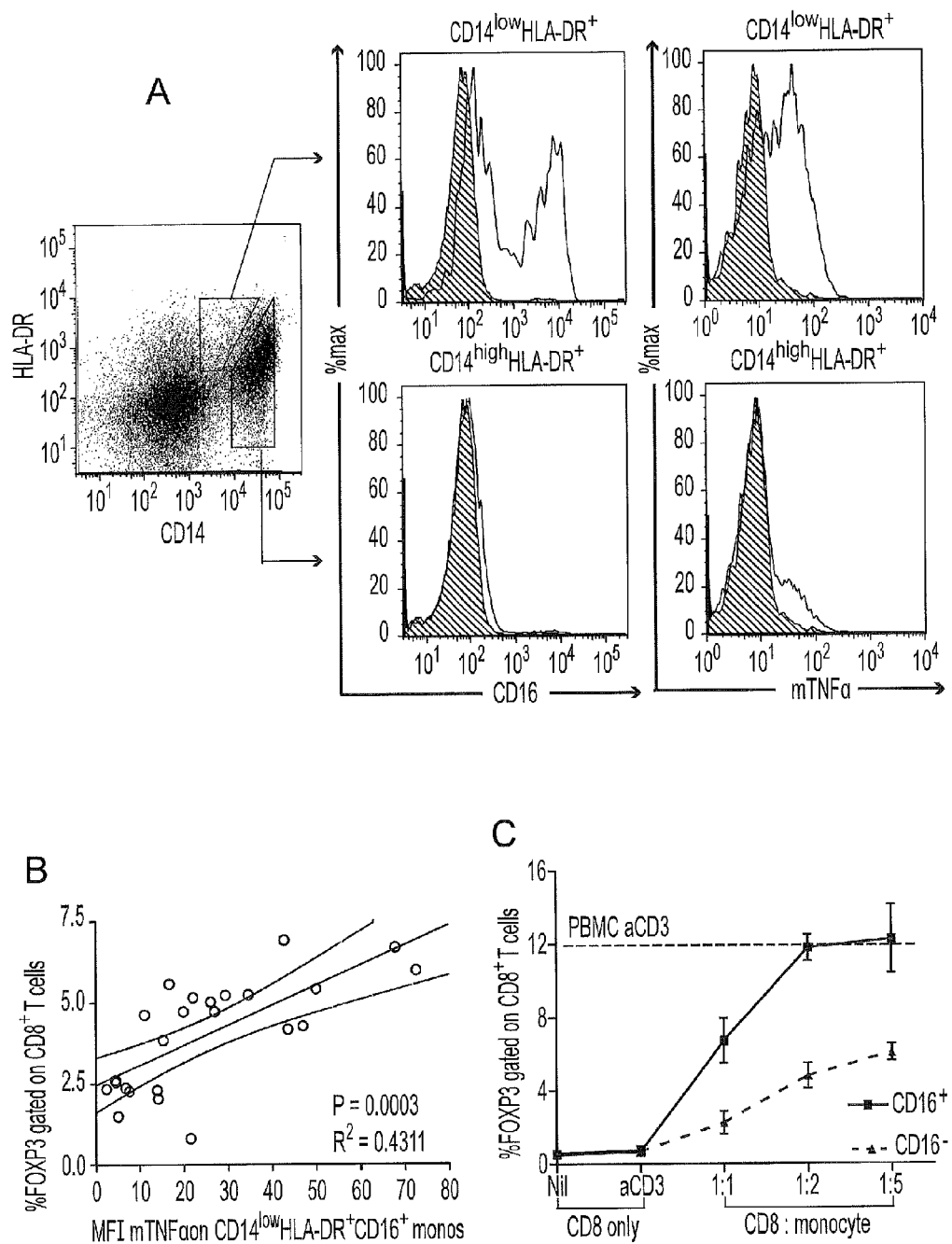
Figure 5:
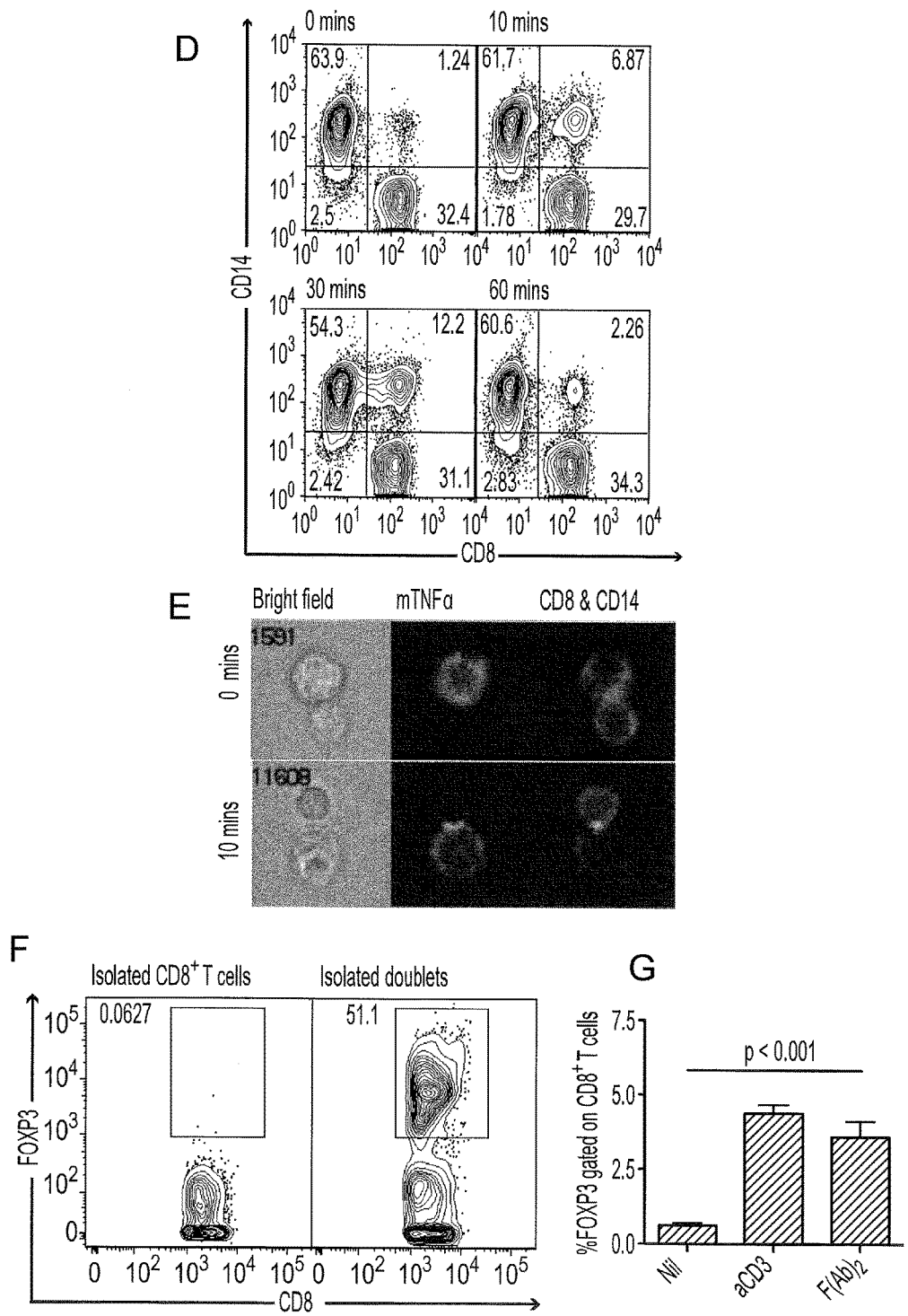

FIG. 5. Induction of FOXP3 is contact-dependent and mediated by CD14$^{low}$HLA-DR+CD16+ monocytes.

(A) Representative flow cytometry plots of RA PBMC stained for CD14, HLA-DR, membrane TNF-α (mTNFα) and CD16. (B) Correlation plots of ex vivo membrane TNF-α expression by CD14$^{low}$HLA-DR+CD16+ monocytes (monos) plotted against % CD8+FOXP3+ Tregs after culture with OKT3 for 24 h. (C) Whole PBMC cultured with 1 µg/ml OKT3 or isolated CD8+ T cells cultured with either CD14$^{low}$HLA-DR+CD16+ (squares) or CD14$^{high}$HLA-DR+CD16- (triangles) sorted monocytes at a ratio of 1 CD8+ T cell to 1, 2 or 5 monocytes for 5 d. Graphs show cumulative data of mean±SEM of % FOXP3 expression by CD8+ T cells. Dotted line represents mean % CD8+FOXP3+ Treg induction from whole PBMC. (D) Isolated CD8+ T cells and monocytes stained for CD8 or CD14 and cultured together with OKT3 for 0, 10, 30 or 60 min. Samples were analyzed by flow cytometry for doublet formation (n=6). (E) Some cultures of CD8+ T cells (green) and CD14+ monocytes (red) were stained for membrane TNF-α at 0 or 10 min and analyzed by ImageStream. Representative images of membrane TNF-α on monocytes in contact with CD8+ T cells. (F) Doublets and CD8+ T cells were sorted and cultured in media for 24 h and analyzed for FOXP3 expression. Representative flow cytometry plots of % FOXP3 expression by CD8+ T cells (n=4). (G) Monocytes fixed in 2% PFA were cultured with autologous monocyte depleted PBMC in the presence of 2 µg/ml F(Ab)$_2$ for 24 h. Histograms show cumulative data of mean±SEM % FOXP3 expression by CD8+ T cells (n=4). One-way repeated measures ANOVA was used for statistical analysis.

Figure 6:
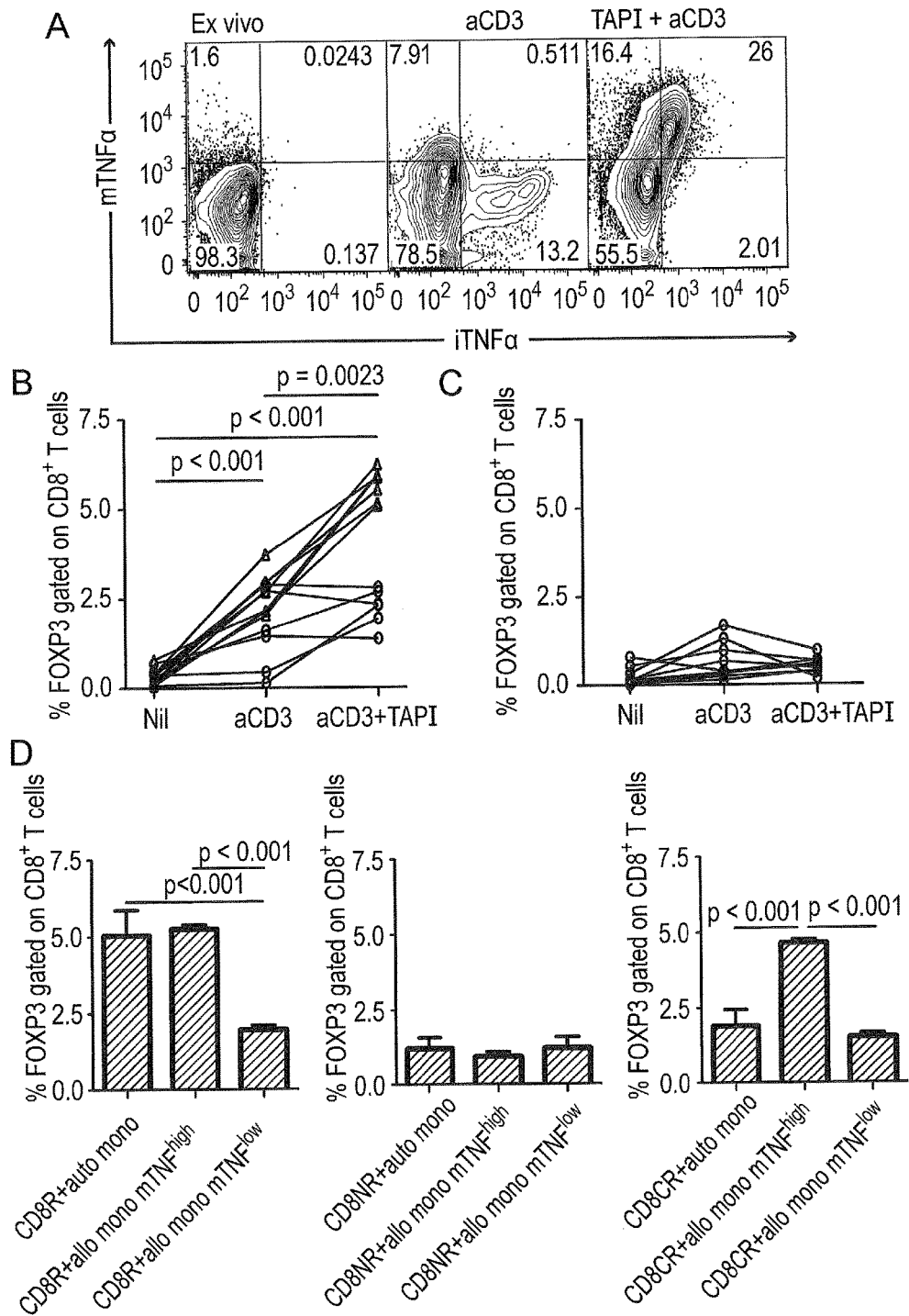

FIG. 6. CD8+ T cells dictate their conversion into CD8+FOXP3+ Treg in the presence of mTNF-α producing monocytes.

RA PBMC cultured with 1 µg/ml OKT3 only, or after pre-incubation with 10 µg/ml TNF-α protease inhibitor (TAPI), for 24 h. (A) Supernatants were removed and replaced with a stimulation mix of PMA, ionomycin and golgi stop for 4 h. Samples were analyzed by flow cytometry. The expression of intracellular TNF-α (iTNFα) and membrane TNF-α (mTNFα) by monocytes (CD14+) was determined. Representative flow cytometry plots shown (n=15). (B) RA PBMC or (C) healthy PBMC cultured with OKT3 only, or after pre-incubation with TAPI, for 24 h and analyzed by flow cytometry for FOXP3 expression by CD8+ T cells. Paired data shown where triangles represent CD8+ T cells that upregulate FOXP3 after monocyte pre-incubation with TAPI, and circles represent CD8+ T cells that do not. One-way repeated measures ANOVA was used for statistical analysis. (d) CD8+ T cells which had induced FOXP3 expression (CD8R) or not (CD8NR) in response to culture with OKT3, or only expressed FOXP3 after pre-incubation with TAPI (CD8CR), were isolated and cultured with isolated autologous (auto) or allogeneic (allo) monocytes expressing high (mTNFhigh) or low (mTNFlow) levels of membrane TNF-α in the presence of OKT3 for 24 h. FOXP3 expression by CD8+ T cells was analyzed by flow cytometry. Histograms show cumulative data of mean percentage±SEM of FOXP3 expression by isolated CD8+ T cells (n=between 8 to 15). One-way repeated measures ANOVA was used for statistical analysis.

Figure 7:
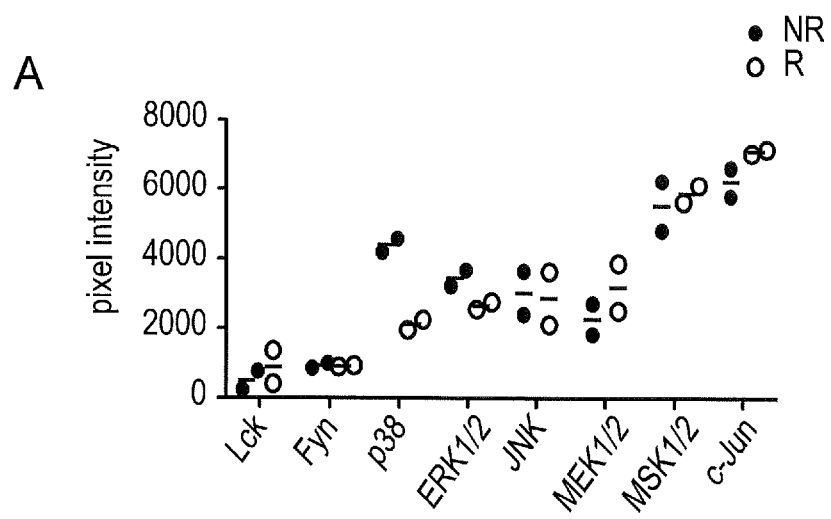
Figure 7:
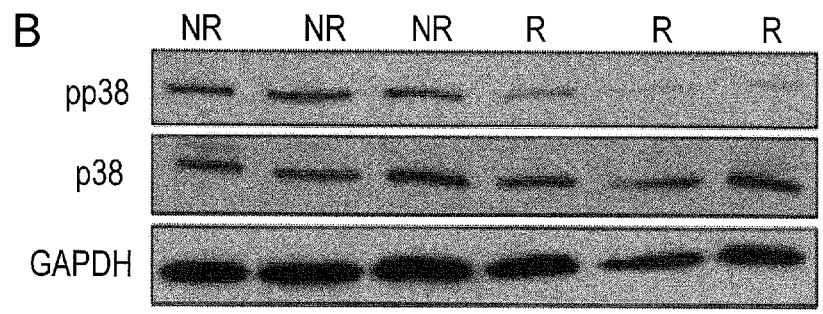
Figure 7:
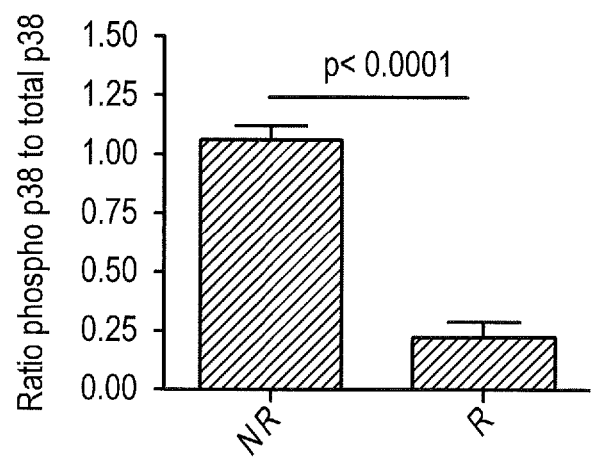
Figure 7:
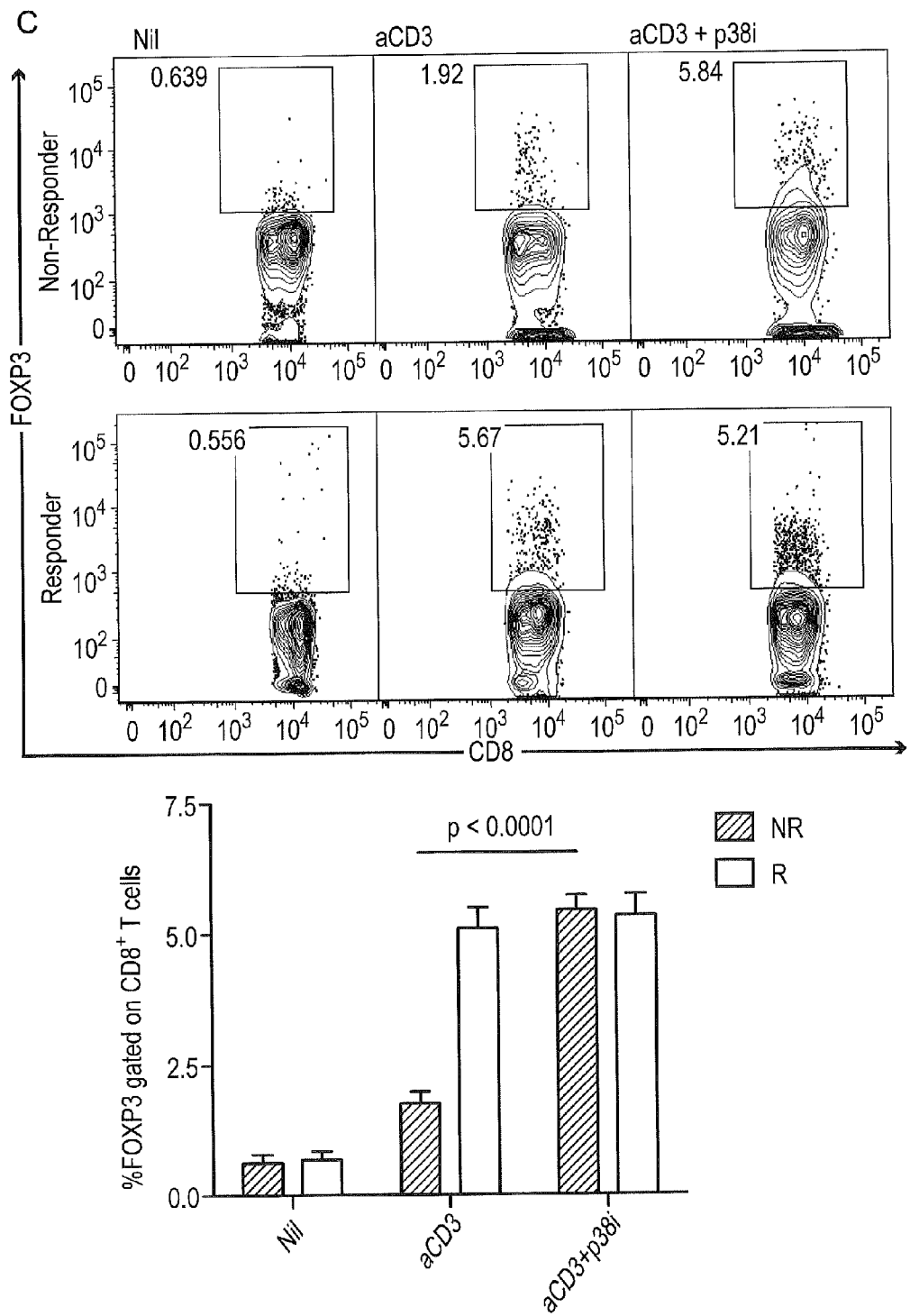

FIG. 7. p38 phosphorylation inhibits CD8+FOXP3+ Treg induction.

CD8+ T cells isolated from RA PBMC, identified previously as responders (R) or non-responders (NR) to CD3-specific stimulation to induce FOXP3 expression, were cultured with 1 µg/ml OKT3, anti-CD28 and anti-TNFRII for 30 min. Cell lysates (25 µg protein) were incubated overnight with membranes from the human phosphorylation kinase array (A) or resolved via western blot (B). (A) Graph shows the mean of duplicates for the 8 phosphorylation targets for 2 responders and 2 non-responders. (B) Representative blots of p38 phosphorylation of 3 responders and 3 non-responders. Graphs show the mean±SEM ratio of the pixel intensity of phosphorylated p38 compared with total p38 (n=5 for each). Two-tailed t-test used for statistical analysis. (C) RA PBMC were cultured with OKT3 (aCD3) alone or pre-incubated with the p38 MAPK inhibitor (p38i), BIRB 796, for 2 h at 37° C. before culture with OKT3 for 24 h then analyzed by flow cytometry. FOXP3 was gated on the CD8+ T cells. Representative plots and cumulative data show the mean±SEM of % FOXP3 expression by CD8+ T cells (n=8 for each). One-way repeated measures ANOVA was used for statistical analysis.

Figure 8:
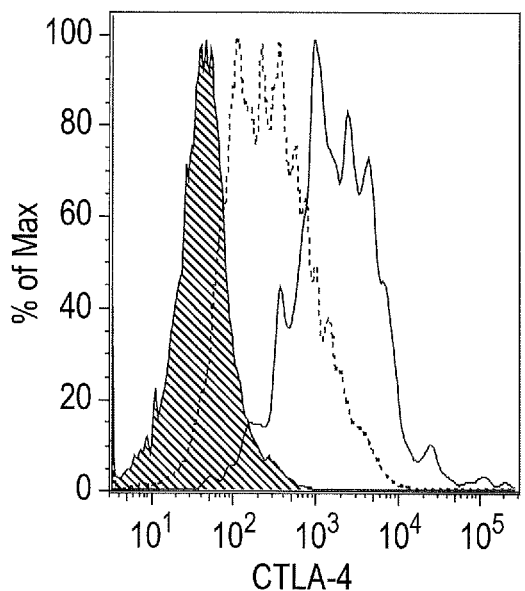
Figure 8:
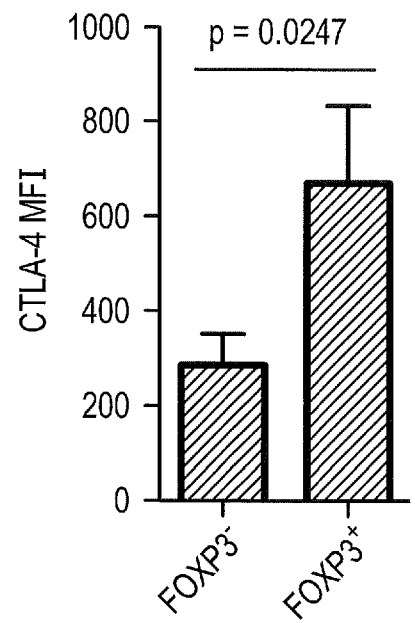
Figure 8:
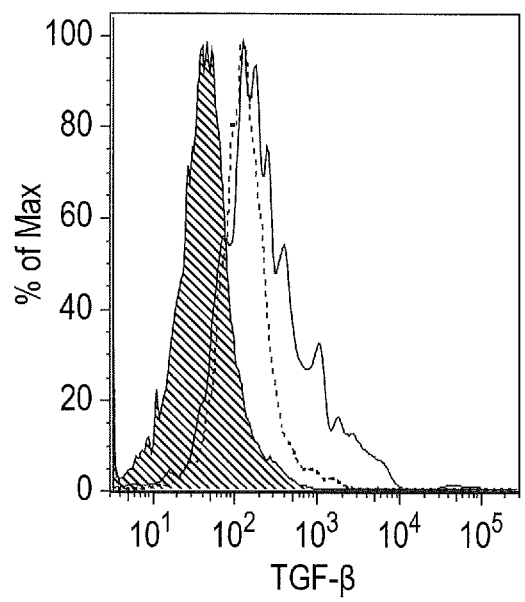
Figure 8:
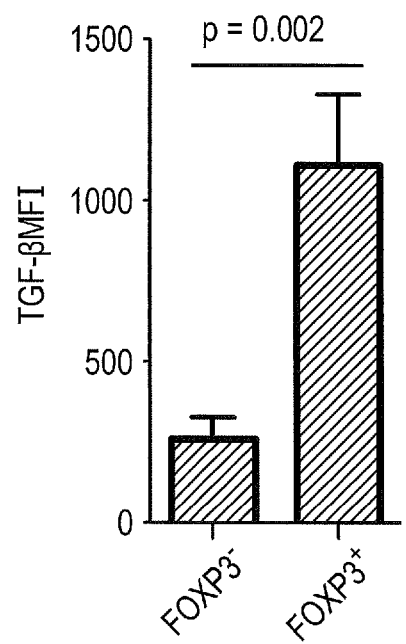
Figure 8:
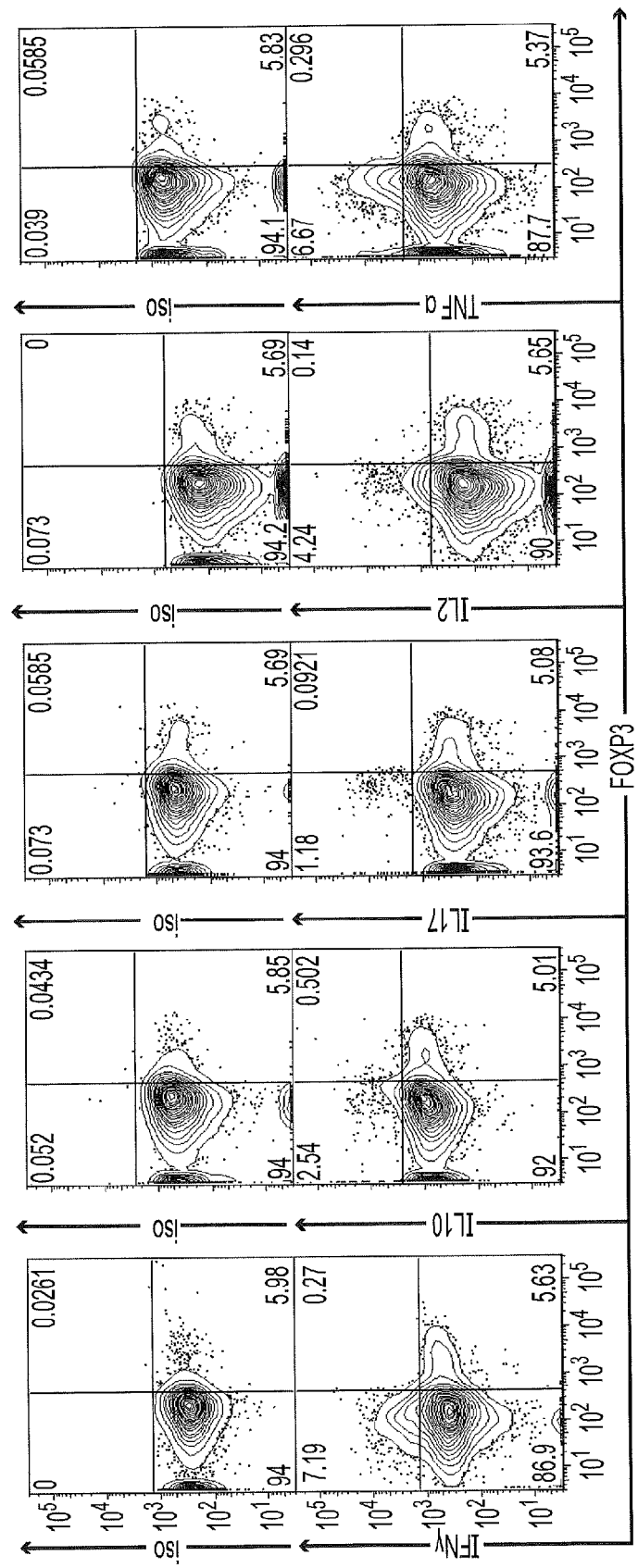

FIG. 8. Induced CD8+FOXP3+ Treg have a regulatory phenotype.

RA PBMC cultured with 1 µg/ml OKT3 for 24 h and further stimulated for 4 h with PMA and ionomycin for cytokine staining. Samples were processed by flow cytometry. CD8+FOXP3+ (FOXP3+) or CD8+FOXP3- (FOXP3-) T cells were analyzed for expression of (A) CTLA-4 and TGF-3 and (B) IFN-γ, IL-10, IL-17, IL-2 and TNF-α. Representative flow cytometry plots shown (n=6). Tinted line represents the isotype control, dotted line represents CD8+FOXP3- T cells, black line represents CD8+FOXP3+ Treg. Cumulative data shows mean±SEM MFI of CTLA-4 (n=4) and TGF-β (n=4). Two-tailed t-test used for statistical analysis.

FIG. 9. Baseline characteristics of RA patients and their prescribed therapies. The mean age and range of patients, the mean C-reactive protein (CRP) and range, the ratio of positive to negative patients for rheumatoid factor (RF) and anti-cyclic citrullinated protein antibodies (CCP) for all patients, those who were untreated and those who were on methotrexate only (Mtx), sulfasalazine only (Ssz) or combined methotrexate and sulfasalazine therapy (Mtx+ssz) is shown for all patients whose PBMC have been used for experiments.

Figure 10:
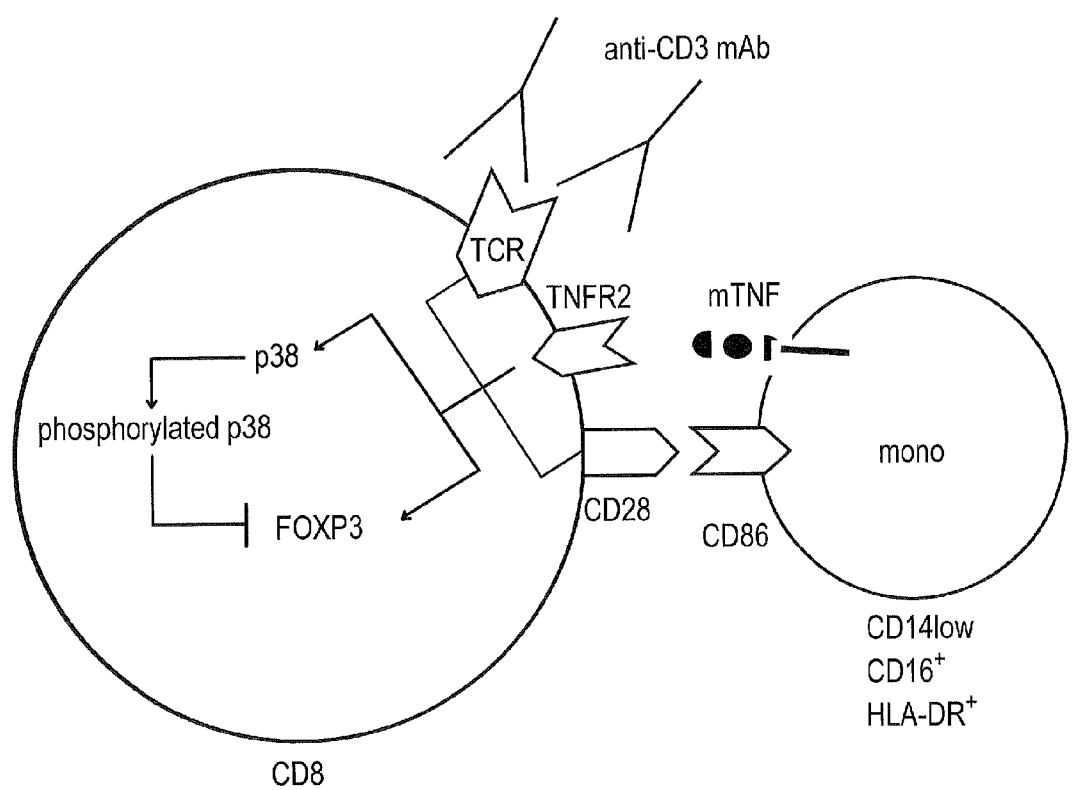

FIG. 10. Schematic diagram of the molecular signalling pathways involved in the induction of CD8+FOXP3+ regulatory T cells.

SUMMARY OF ASPECTS OF THE INVENTION

The mechanism of function of CD3-specific mAbs has been attributed to TCR blockade and internalization, induction of anergy and depletion of CD4+ effector T cells. However, their tolerogenic effects require the induction of functional regulatory T cells (Treg).

Some studies have identified that anti-CD3 therapy expands or induces CD8+ T cells expressing FOXP3+. The mechanism of induction of these cells is undetermined.

The present inventors used RA as a model of TNF-α driven inflammation to investigate CD8+FOXP3+ Treg induction in response to anti-CD3 mAb. They have identified a previously unknown mechanism of CD8+ Treg induction, which is mediated by membrane TNF-α expressed on CD14$^{low}$HLA-DR+CD16+ monocytes. They have also identified that patients vary in their induction of CD8+FOXP3+ Tregs in response to anti-CD3 mAb therapy, governed by differences in the level of phosphorylation of p38. A combination therapy using anti-CD3 mAb with a p38 inhibitor increases the efficacy of anti-CD3 mAb therapy and the proportion of responding patients.

Thus, in a first aspect, the present invention provides a method for inducing CD8+FOXP3+ regulatory T cells in a subject which comprises administering to the subject:
(i) a first agent which inhibits p38 phosphorylation; and
(ii) a second agent which stimulates T-cell receptor (TCR) signalling.

The agents may be administered simultaneously, sequentially or separately. For sequential or separate administration, the first and second agents may be administered in either order.

The first agent may be a p38 inhibitor selected from the group consisting of Tocriset, Pamapimod, AMG-548, SD282, SB239063, SB203580, SB220025, SKF86002, PD169316, PH-797804, SB202190, SC68376, VX702, VX745, R130823, AMG548, BIRB796, SC10469, SCIO323, FR167653, MW12069ASRM, SD169, RWJ67657, and ARRY79.

The first agent may be BIRB 796.

The second agent may be an anti-CD3 antibody, for example an anti-CD3 antibody selected from the following: OKT3, HIT3A, UCHT1, Teplizumab and Otelixizumab.

In a second aspect, the present invention provides a method for treating and/or preventing an autoimmune and/or inflammatory condition in a subject which comprises inducing CD8+FOXP3+ regulatory T cells in a subject by a method according to the first aspect of the invention.

The autoimmune and/or inflammatory condition may, for example, be diabetes, psoriatic arthritis, or rheumatoid arthritis.

The subject may be poorly responsive to anti-CD3 therapy alone.

In a third aspect, the present invention provides a composition which comprises:
(i) a first agent which inhibits p38 phosphorylation as defined above; and
(ii) a second agent which stimulates T-cell receptor (TCR) signalling as defined above.

In a fourth aspect, the present invention provides a kit which comprises:
(i) a first agent which inhibits p38 phosphorylation in CD8+ T cells as defined above; and
(ii) a second agent which stimulates T-cell receptor (TCR) signalling as defined above
for simultaneous, sequential or separate administration to a subject.

In the kit, one of the agents may be in the form of a composition of the third aspect of the invention. Alternatively, the kit may comprise the first agent, the second agent and a composition according to the third aspect of the invention.

In other aspects, the present invention also provides:
(i) a composition according to the third aspect of the invention a kit according to the fourth aspect of the invention for use in inducing CD8+FOXP3+ regulatory T cells in a subject;
(ii) a composition according to the third aspect of the invention a kit according to the fourth aspect of the invention for use in treating and/or preventing an autoimmune and/or inflammatory condition in a subject;
(iii) the use of a first agent and a second agent as defined above in the manufacture of a medicament for inducing CD8+FOXP3+ regulatory T cells in a subject; and
(iv) the use of a first agent and a second agent as defined above in the manufacture of a medicament for treating and/or preventing an autoimmune and/or inflammatory condition in a subject.

The present invention also provides the use of an agent which inhibits p38 phosphorylation in CD8+ T cells to enhance the efficacy of an anti-CD3 antibody to treat and/or prevent an autoimmune and/or inflammatory condition in a subject.

The autoimmune and/or inflammatory condition may, for example, be rheumatoid arthritis. The subject may be poorly or non-responsive to anti-CD3 therapy alone.

The agent which inhibits p38 phosphorylation in CD8+ T cells may increase the proportion of patients that respond to the anti-CD3 antibody.

The present invention also provides a method for patient stratification which comprises the step of examining FOXP3 expression on CD8+ T cells following anti-CD3 stimulation.

The method may comprise the following steps:
(i) incubation of a CD8+ T cell-containing sample from the patient with an anti-CD3 antibody; and
(ii) examining FOXP3 expression on CD8+ T cells before and after step (i).

A patient showing no significant increase in FOXP3 expression on CD8+ T cells following anti-CD3 stimulation may be considered to be a "non-responder".

A "non-responder" patient may be considered suitable for treatment using a method according to the first or second aspects of the invention.

As explained above, the present inventors have found that patients vary in their induction of CD8+FOXP3+ Tregs in response to anti-CD3 mAb therapy, governed by differences in the level of phosphorylation of p38. This explains why, despite promising results from animal models, treatment of inflammatory autoimmune conditions with anti-CD3 antibodies has met with limited success, as a significant proportion of patients show little or no response. Now that the present inventors have elucidated the molecular pathways behind CD8+FOXP3+ Tregs induction. By pre-treating patients with an agent which inhibits p38 phosphorylation, or using a combined treatment, CD8+ T cells can be made responsive to TCR signalling, so that anti-CD3 antibody therapy is effective in inducing CD8+FOXP3+ Treg cell. This means improved efficacy of anti-CD3 antibody therapy for all patients, and makes previously poorly or non-responsive patients responsive to treatment with anti-CD3 antibodies.

DETAILED DESCRIPTION

CD8+FOXP3+ Regulatory T Cells (TREG)

The present inventors have described a potent CD8+ FOXP3+ regulatory T cell (Treg) population that is induced in some patients by T cell receptor stimulation (TCR) using anti-CD3 antibodies.

These Treg cells express TGF-β and CTLA-4 and suppress CD4+ T cell proliferation and IL-17 and IFN-γ production.

Monocytes are involved in the induction of FOXP3 expression following TCR activation, providing co-stimulation through CD86 and membrane TNF-α (see FIG. 10).

The present invention provides a method for inducing FOXP3 expression in CD8+ T cells in a subject, to produce CD8+FOXP3+ Treg cells.

FOXP3+ expression may be induced in CD8+ T cells at a site of inflammation.

Methods for analysing the level of FOXP3+ expression by CD8+ T cells, or the numbers of CD8+FOXP3+ Treg cells in a subject, or a sample from a subject, are known in the art.

The Examples provided herein describe the use of flow cytometry to analyse FOXP3+(and CD8+) expression in PBMC.

Inhibition of p38 Phosphorylation

The present inventors have shown that inhibition of p38 phosphorylation in CD8+ T cells makes those cells more permissive to FOXP3 induction.

Anti-CD3 induces CD8 regulatory cells with potent suppressive capacity in PBMC from RA patients, but only in a proportion of individuals. Inhibition of p38 can convert "non-responders" to responders and an increase in their regulatory T cell numbers.

The mitogen-activated protein kinase (MAPK) p38 is a Ser/Thr kinase, originally isolated from lipopolysaccharide-stimulated monocytes. In the present document, the terms "p38" and "P38 MAP kinase" are used interchangeably.

P38 MAP kinase is responsive to stress stimuli, such as cytokines, ultraviolet irradiation, heat shock, and osmotic shock, and are involved in cell differentiation, apoptosis and autophagy.

It is involved in the biosynthesis of cytokines such as TNFα and IL-1β at the transcriptional and translational level. It represents a point of convergence for multiple signaling processes that are activated during inflammation.

Mitogen-activated protein kinase kinase 3(MKK3) and 6 (MKK6) activate p38 MAP kinase by phosphorylation at Thr-180 and Tyr-182. Activated p38 MAP kinase phosphorylates and activates MAPKAP kinase 2 and phosphorylates the transcription factors ATF2, Mac and MEF2. p38 also has been shown to phosphorylate post-transcriptional regulating factors like TTP.

Phosphorylation of P38 may be inhibited by inhibitors such as Tocriset, Pamapimod, AMG-548, SD282, SB239063, SB203580, SB220025, SKF86002, PD169316, PH-797804, SB202190, SC68376, VX702, VX745, R130823, AMG548, BIRB796, SCIO469, SCIO323, FR167653, MW12069ASRM, SD169, RWJ67657, and ARRY797.

The inhibitors AMG-548, BIRB-796, SCIO-469, SCID-323 and VX-702 have been tested in clinical trials.

Stimulation of TCR Signalling

The TCR (T-Cell Receptor) is a complex of integral membrane proteins that participates in the activation of T-Cells in response to the presentation of antigen. Stimulation of TCR is triggered by MHC (Major Histocompatibility Complex) molecules on antigen presenting cells that present antigenic peptides to TCR complexes and induce a series of intracellular signaling cascades. Engagement of the TCR initiates positive (signal-enhancing) and negative (signal-attenuating) cascades that ultimately result in cellular proliferation, differentiation, cytokine production, and/or activation-induced cell death.

TCR is composed of six different chains that form the TCR heterodimer responsible for ligand recognition. CD3 molecules (CD3-Gamma, Delta, Epsilon and Zeta), which are assembled together with the TCR heterodimer, possess a characteristic sequence motif for tyrosine phosphorylation, known as ITAMs (Immunoreceptor Tyrosine-based Activation Motifs). The TCR polypeptides themselves have very short cytoplasmic tails, and all proximal signaling events are mediated through the CD3 molecules.

T-Cell activation is initiated by the interaction of the TCR with antigenic peptides complexed to MHC-II molecules, and accessory proteins essential for MHC-II. TCR-CD3 complex interaction plays an important role in mediating cell recognition events. TCR engagement by antigens triggers the tyrosine phosphorylation of the ITAMs, present in the TCR-associated CD3-Zeta subunits. Such ITAMs function by orchestrating the sequential activation of the Src-related PTKs: Lck and Fyn, which initiate TCR signaling, followed by that of ZAP70, which further amplifies the response. Lck is activated by the interaction of MHC-II and CD4 or CD8. These various PTKs induce tyrosine phosphorylation of several polypeptides, including the transmembrane adaptors: LAT (Linker Activator for T-Cells) and TRIM (T-Cell Receptor Interacting Molecule). Protein tyrosine phosphorylation subsequently leads to the activation of multiple pathways, including ERK (Extracellular Signal Regulated Kinase), JNK (c-Jun N-terminal Kinase), NF-KappaB (Nuclear Factor-KappaB) and NFAT (Nuclear Factor of Activated T-Cells) pathways, which ultimately induce effector functions.

TCR activation is regulated by various costimulatory receptors. CD28 provides an essential co-stimulatory signal during T-cell activation, which augments the production of IL-2 (Interleukin-2), increases T-Cell proliferation and prevents the induction of anergy and cell death. Once ligated by B7-1 or B7-2, CD28 provides the T-Cell with an initial adhesion capable of approximating the T-Cell and Antigen Presenting Cell membranes. Besides CD28, many other transmembrane receptors also modulate specific elements of TCR signaling. CD45 (CD45 Antigen) is one such receptor which regulates TCR signaling by modulating the phosphorylation state of the tyrosine kinases like Lck and Fyn, and antagonizing the inhibitory impact of inhibitory proteins, thereby favoring T-Cell activation. Lck is also activated by CD28. Activated Lck in turn activates the phosphorylation and activation of the TCR-CD3 complex and consequently, the tyrosine kinases: Fyn and ZAP70 (Zeta-Chain (TCR) Associated Protein Kinase of 70 kDa).

The second agent may stimulate T cell signalling by interacting with one or more molecules involved in T cell activation, such as CD3, Lck, Fyn, ZAp70, LAT or TRIM.

The second agent may be a CD3 agonist. It may cause tyrosine phosphorylation of ITAMs present CD3-Zeta subunits.

Anti-CD3 Antibodies

The second agent may be an anti-CD3 antibody.

Previously described anti-CD3 antibodies include OKT3, HIT3A, muromonab-CD3, otelixizumab, teplizumab and visilizumab.

The term "antibody" includes intact antibodies, fragments of antibodies, e.g., Fab, F(ab') 2 fragments, and intact antibodies and fragments that have been mutated either in their constant and/or variable region (e.g., mutations to produce chimeric, partially humanized, or fully humanized antibodies, as well as to produce antibodies with a desired trait, e.g., enhanced CD3 binding).

The term "fragment" refers to a part or portion of an antibody or antibody chain comprising fewer amino acid residues than an intact or complete antibody or antibody chain. Fragments can be obtained via chemical or enzymatic treatment of an intact or complete antibody or antibody chain. Fragments can also be obtained by recombinant means. Binding fragments include Fab, Fab', F(ab') 2, Fabc, Fd, dAb, Fv, single chains, single-chain antibodies, e.g., scFv, single domain antibodies, and an isolated complementarity determining region (CDR).

Antibody-like molecules include the use of CDRs separately or in combination in synthetic molecules such as SMIPs and small antibody mimetics. Specificity determining regions (SDRs) are residues within CDRs that directly interact with antigen. The SDRs correspond to hypervariable residues. CDRs can also be utilized in small antibody mimetics, which comprise two CDR regions and a framework region.

Autoimmune and/or Inflammatory Condition

In a second aspect, the present invention provides a method for treating and/or preventing an autoimmune and/or inflammatory condition.

A method for the prevention of an autoimmune or inflammatory disease relates to the prophylactic use of the first and second agents. Herein the agent(s) may be administered to a subject who has not yet contracted an autoimmune and/or inflammatory disease and/or who is not showing any symptoms of the disease to prevent or impair the cause of the disease or to reduce or prevent development of at least one symptom associated with the disease. The subject may have a predisposition for, or be thought to be at risk of developing, an autoimmune disease.

A method for the treatment of an autoimmune and/or inflammatory disease relates to the therapeutic use of the first and second agents. Herein the agent(s) may be administered to a subject having an existing disease or condition in order to lessen, reduce or improve at least one symptom associated with the disease and/or to slow down, reduce or block the progression of the disease.

Chronic inflammation in diseases such as rheumatoid arthritis (RA), Crohn's disease, inflammatory bowel syndrome (IBS) and psoriasis are mediated by pro-inflammatory cytokines such as tumour necrosis factor (TNF) α, IL-1β, IL-6 and IL-8. In particular, TNF-α plays a key role in the pathogenesis of RA and other autoimmune inflammatory diseases. TNFα is produced by synovial macrophages and are present in rheumatoid synovial fluid where it affects cell proliferation, collagenase production, adhesion molecule expression and chemokine production. The milieu in the rheumatoid joint eventually leads to dysregulation and activation of synovial fibroblasts, which in turn provides a positive feedback loop to perpetuate synovial inflammation.

The method of the invention may be used to treat and/or prevent a condition such as an inflammatory condition or an autoimmune disease.

The condition may involve TNF-α driven inflammation.

The condition may, for example be one of the following: pancreatitis, type I diabetes (IDDM), Graves Disease, inflammatory bowel disease (IBD), Crohn's Disease, ulcerative colitis, irritable bowel syndrome, multiple sclerosis, rheumatoid arthritis, juvenile idiopathic arthritis, diverticulosis, systemic lupus erythematosus, psoriasis, ankylosing spondylitis, scleroderma, systemic sclerosis, psoriatic arthritis, osteoarthritis, atopic dermatitis, vitiligo, Sjogren's syndrome, glomerulonephritis, IgA nephropathy, atopic dermatitis and anti-phospholipid syndrome.

Administration

In the method of the first and second aspects of the invention, the first agent may be administered to a subject, followed by the second agent.

Alternatively, the two agents may be administered simultaneously, for at least part of the treatment.

For example, the subject may be given the first agent, either as a single treatment or a course of treatment; followed by the second agent, optionally in combination with the first agent, either as a single treatment or a course of treatment.

The present inventors have observed that CD8$^+$FOXP3$^+$ Treg were increased in the periphery during chronic inflammation and that further induction from CD8$^+$FOXP3$^-$ effector T cells could occur following TCR stimulation provided by anti-CD3 mAbs. However, this induction is governed by the lack of phosphorylation of p38 on CD8$^+$ T cells. It is therefore important to inhibit p38phosphorylation in CD8+ T cells before and/or at the same time as providing TCR stimulation, so that the CD8+ T cells are "ready" to respond in a positive way to TCR stimulation.

Typically, a physician will determine the actual dosage which will be most suitable for an individual subject and it will vary with the age, weight and response of the particular patient.

Each agent may be administered with a pharmaceutically acceptable carrier, diluent, excipient or adjuvant. The choice of pharmaceutical carrier, excipient or diluent can be selected with regard to the intended route of administration and standard pharmaceutical practice. The pharmaceutical compositions may comprise as (or in addition to) the carrier, excipient or diluent, any suitable binder(s), lubricant(s), suspending agent(s), coating agent(s), solubilising agent(s), and other carrier agents.

Where appropriate, the agent(s) or composition(s) can be administered by any one or more of: inhalation, in the form of a suppository or pessary, topically in the form of a lotion, solution, cream, ointment or dusting powder, by use of a skin patch, orally in the form of tablets containing excipients such as starch or lactose, or in capsules or ovules either alone or in admixture with excipients, or in the form of elixirs, solutions or suspensions containing flavouring or colouring agents, or they can be injected parenterally, for example intracavernosally, intravenously, intramuscularly or subcutaneously. For parenteral administration, the compositions may be best used in the form of a sterile aqueous solution which may contain other substances, for example enough salts or monosaccharides to make the solution isotonic with blood. For buccal or sublingual administration the compositions may be administered in the form of tablets or lozenges which can be formulated in a conventional manner.

Subject

The subject may be a mammalian subject such as a human.

The subject may have an inflammatory and/or autoimmune condition, or be thought to be at risk from contracting an inflammatory and/or autoimmune condition, because of, for example, family history or the condition or the presence of genetic or phenotypic (e.g. biomarkers) associated with the condition.

The subject may have been considered a "poor responder" by the method of patent stratification of the present invention described below.

The subject may have been previously treated with an anti-CD3 antibody treatment but not shown significant improvement in their disease condition.

Composition

The present invention also provides a composition comprising the first and second agents.

As explained above, the two agents may be administered simultaneously for at least part of the treatment regimen. The composition of the invention may be used for such treatments or part thereof.

In one embodiment, the treatment comprises two phases: a first phase, where the first agent is administered alone, followed by a second phase, where the first and agents are administered together.

The composition may be suitable for administration by any of the routes mentioned above, such as oral or intravenous administration.

Kit

The present invention also provides a kit which comprises the first and second agents for simultaneous, sequential or separate administration.

The kit may comprise: the first agent, the second agent and/or a composition comprising the first and second agents.

The provision of the agents or compositions in kit form facilitates their use in a multiple phase treatment, as described above. It is also useful where the agents or compositions have different administration routes, for example one orally and one by i.v. injection.

The kit may also comprise instructions for use.

Method for Patient Stratification

The present invention also provides a method for patient stratification which involves examining FOXP3 expression on CD8+ T cells following anti-CD3 stimulation.

The patient may have an inflammatory condition or an autoimmune disease.

The method may involve contacting a CD8+ T cell-containing sample from the patient with an anti-CD3 antibody and analysing FOXP3 expression. FOXP3 expression may be analysed by method known in the art such a flow cytometry.

Alternatively the method may involve stimulating TCR signalling in vivo, for example by administering an anti-CD3 antibody, and then analysing FOXP3 expression by CD8+ T cells in the subject or in a sample from the subject.

A subject showing little increase in FOXP3 expression on CD8+ T cells following anti-CD3 stimulation is considered to be a "poor-responder", whereas a subject showing no significant increase in FOXP3 expression on CD8+ T cells following anti-CD3 stimulation is considered to be a "non-responder".

Relative increases in expression may be assessed by comparison with a negative control, such as a healthy subject, and/or a positive control, such as a subject which is known to be responsive to treatment with anti-CD3 antibodies, or who has been pre-treated with a p38 inhibitor.

A "non-responder" or "poor-responder" patient may be considered suitable for treatment using a method according to the first and second aspects of the invention.

The invention will now be further described by way of Examples, which are meant to serve to assist one of ordinary skill in the art in carrying out the invention and are not intended in any way to limit the scope of the invention.

EXAMPLES

Example 1

Inflammatory Arthritis is Associated with Increased $CD8^+FOXP3^+$ T Cells

Figure 1:
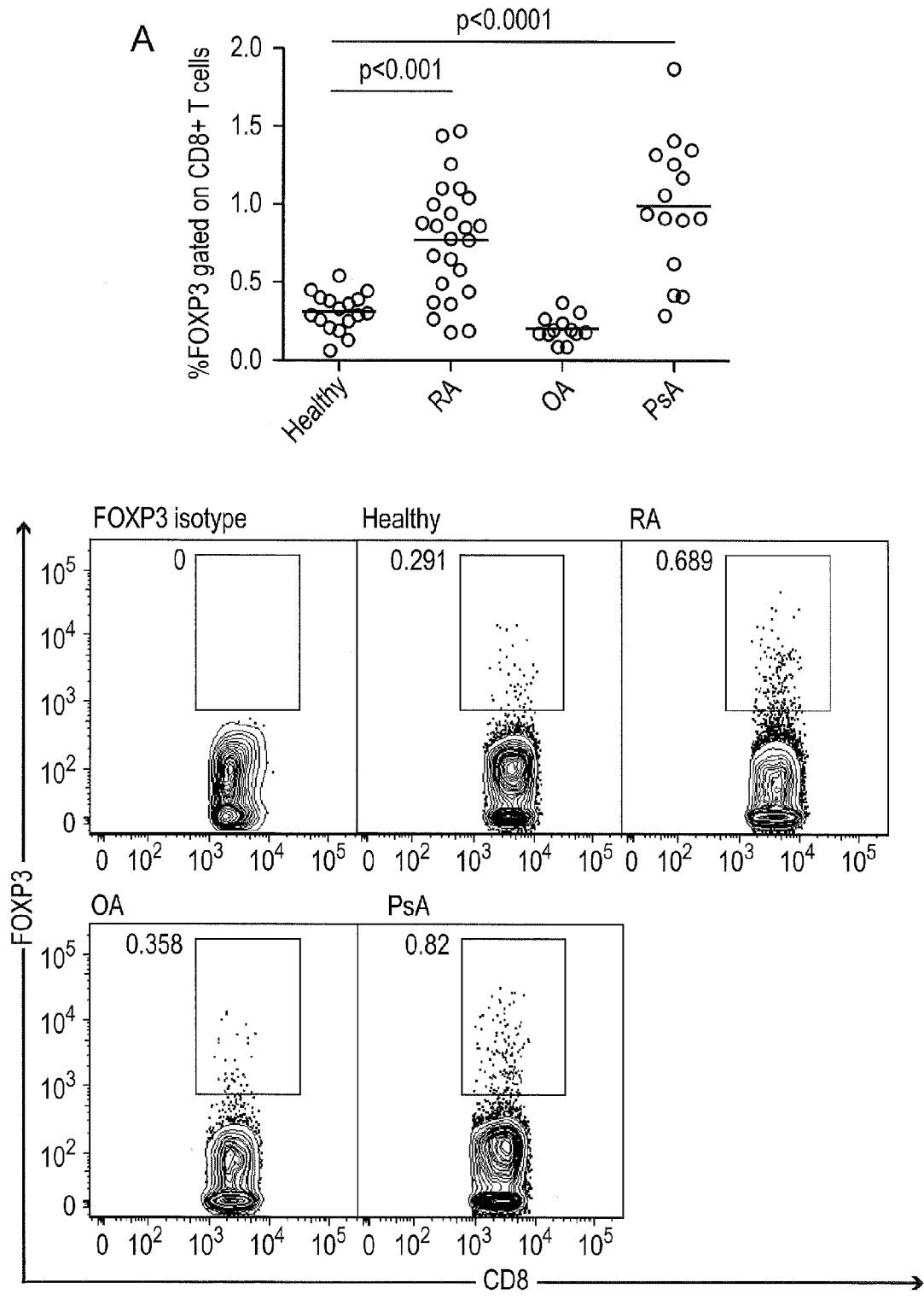
FIG. 1. Inflammatory arthritis is associated with increased $CD8^+FOXP3^+$ T cells.
Figure 1:
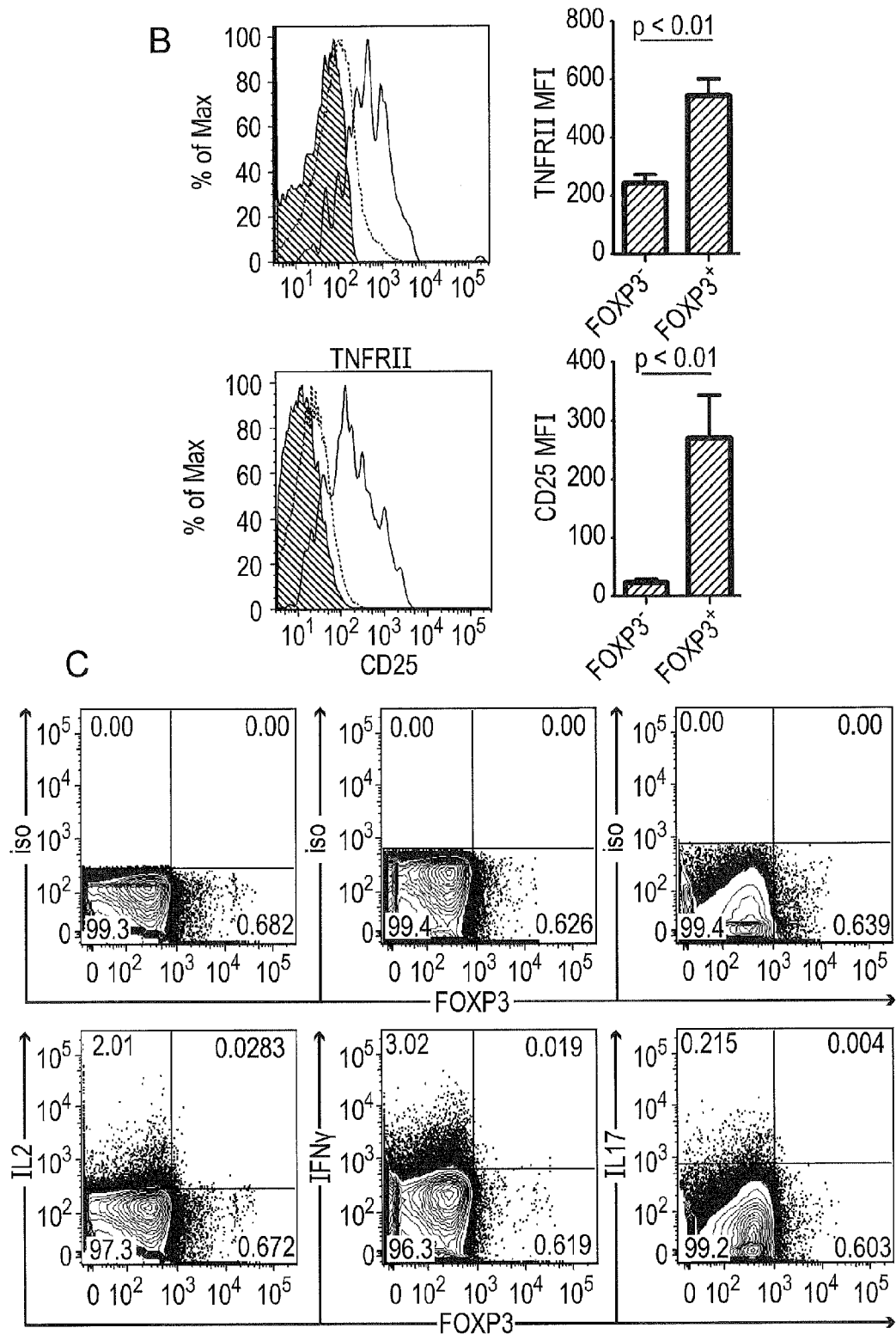

It was found that patients with rheumatoid or psoriatic arthritis had significantly increased percentages of $CD8^+ FOXP3^+$ T cells in peripheral blood (PB) compared to patients with a non-inflammatory arthritis (osteoarthritis) or healthy donors (FIG. 1A).

Analysis of the surface markers and cytokine profile of $CD8^+FOXP3^+$ T cells from patients with RA confirmed that they had a regulatory phenotype. This study revealed increased expression of CD25 and TNFRII (FIG. 1B) and negligible production of IFN-γ, IL-2 and IL-17 (FIG. 1C).

Example 2

T Cell Receptor Stimulation Induces $CD8^+FOXP3^+$ Tregs from RA PBMC

In order to investigate whether anti-CD3 mAb would induce or expand $CD8^+FOXP3^+$ Tregs in RA, PBMC from patients with RA were incubated with different clones of anti-CD3 mAbs: OKT3, HIT3A, UCHT1 and Otelixizumab (a kind gift from GlaxoSmithKline). It was found that a dose of 1 μg/ml OKT3 successfully increased levels of FOXP3 expression by $CD8^+$ T cells after 24 h. All anti-CD3 mAbs tested induced expression of FOXP3 to a similar level in $CD8^+$ T cells (FIG. 2A).

It was then investigated whether anti-CD3 mAb was expanding the pre-existing $CD8^+FOXP3^+$ Treg population or inducing de novo FOXP3 expression. $CD8^+FOXP3^+$ T cells constitutively express CD25, thus $CD8^+CD25^+$ T cells were depleted from RA PBMC and the depleted PBMC were cultured with anti-CD3 mAb for 24 h. This revealed that anti-CD3 mAb induced de novo FOXP3 expression by $CD8^+FOXP3^-$ T cells (FIG. 2B). Subsequent culture of $CD8^+CD25^+$ T cells with RA PBMC depleted of $CD8^+ CD25^-FOXP3^-$ T cells confirmed that anti-CD3 mAb was not expanding pre-existing $CD8^+FOXP3^+$ Treg (FIG. 2B).

Cultures of RA PBMC with anti-CD3 mAb for 5 days revealed sustained and increased FOXP3 expression by $CD8^+$ T cells. Strikingly, variation was observed in the ability of $CD8^+$ T cells from different patients to induce FOXP3 expression in response to anti-CD3 mAb (FIG. 2C). After 5 d of culture, patients could be divided into three groups, based on the percentage of FOXP3 expression by $CD8^+$ T cells: non-responders, responders and high-responders. The pattern of $CD8^+FOXP3^+$ Treg induction by anti-CD3 mAb did not correlate with the RA patients' clinical features: C-reactive protein (CRP) levels, rheumatoid factor (RF) or anti-cyclic citrullinated peptide (ACPA) status or current medication (data not shown).

Characterization of the induced CD8+FOXP3+ Tregs revealed high expression of CD25 and TNFRII in addition to CTLA-4 and TGF-β (FIG. 2D and FIG. 8A). CD8+ FOXP3− T cells were the foremost producers of IL-2, IL-17, IFN-γ and TNF-α. IL10 production was detectable only in CD8+FOXP3− T cells (FIG. 8B). The regulatory properties of the induced CD8+FOXP3+ Treg were tested by examining their effect on CD4+ T cell proliferation and cytokine production. After 3 d of culture with anti-CD3 mAb followed by 2 d resting the cells in media, CD8+FOXP3+ Tregs were isolated from the PBMC of RA patients via their expression of CD25. Autologous whole PBMC were then depleted of CD8+ T cells and stained with CFSE and stimulated with 1 µg/ml staphylococcal enterotoxin B (SEB). They were then co-cultured with induced CD8+CD25+FOXP3+ T cells, CD8+CD25−FOXP3− T cells or the depleted CD8+ T cells at various ratios for 3 or 5 d. CD8+CD25+FOXP3+ Treg restrained CD4+ T cell proliferation at 3 d (FIG. 3A) and maintained their suppressive ability after 5 d in culture (FIG. 3B) in contrast to their CD25− counterparts. Moreover, CD8+CD25+FOXP3+ Treg, but not CD8+CD25−FOXP3− T cells, could suppress IL-17 and IFN-γ production in vitro (FIG. 3C).

Example 3

Monocytes Support CD8+FOXP3+ Treg Induction

In order to investigate whether the cytokines TNF-α, IL-6 and IL-1β are important for CD8+FOXP3+ Treg induction, those cytokines were neutralised in PBMC cultured with anti-CD3 mAb. Among them, only TNF-α is responsible for approximately 50% of FOXP3 expression by CD8+ T cells at 24 h (FIG. 4A).

In order to determine the source of TNF-α; CD4+ T cells, B cells or monocytes were depleted from RA PBMC and then cultured with anti-CD3 mAb. It was found that induction of CD8+FOXP3+ Tregs was unaffected by CD4+ T cell and B cell removal but completely abolished by monocyte depletion (FIG. 4B). Given the complete absence of FOXP3 induction following monocyte depletion compared to a 50% reduction following TNF-α blockade, additional factors were sought in addition to TNF-α that promote CD8+ FOXP3+ Treg induction. Block CD80 and/or CD86 in PBMC cultured with anti-CD3 mAb revealed that CD86 was responsible for approximately 50% of CD8+FOXP3+ Treg induction (FIG. 4C). Finally, combined CD86 blockade and TNF-α neutralisation in whole PBMC cultured with anti-CD3 mAb successfully ablated CD8+FOXP3+ Treg induction, similar to the depletion of monocytes (FIG. 4D).

It was then investigated whether it is possible to replace the signals monocytes provide to induce FOXP3 expression by CD8+ T cells with agonist antibodies. Agonist antibodies to CD28 and TNFRII were used in RA PBMC depleted of monocytes. It was found that the combined agonist antibodies, in conjunction with anti-CD3 mAb, successfully induced CD8+FOXP3+ Treg to comparable levels of whole PBMC (FIG. 4E), thus confirming that FOXP3 expression is induced in CD8+ T cells in response to TCR, CD28 and TNFRII signals.

Example 4

Monocytes Interact Directly with CD8+ T Cells Via Membrane TNF-α to Induce FOXP3 Expression Two distinct monocyte subsets are known to exist in humans which can be identified based on their expression of CD14, CD16 and HLA-DR. It was found that that CD14$^{low}$HLA-DR+ monocytes expressed high levels of CD16 and membrane TNF-α (FIG. 5A). Interestingly, a correlation was also observed between the level of expression of membrane TNF-α by CD14$^{low}$HLA-DR+CD16+ monocytes and FOXP3 induction by CD8 T cells after culture with anti-CD3 mAb (FIG. 5B). In contrast, FOXP3 induction did not correlate with the level of CD86 expression on CD14$^{low}$HLA-DR+CD16+ monocytes (data not shown).

In order to elucidate the relationship between membrane TNF-α expression by monocyte subpopulations and the induction of CD8+FOXP3+ Treg, CD8+ T cells from RA PBMC were isolated and co-cultured with isolated CD14$^{low}$HLA-DR+CD16+ or CD14$^{high}$HLA-DR+CD16− monocytes in the presence of anti-CD3 mAb for 5 days. Although both monocyte populations could induce CD8+ FOXP3+ Tregs, CD14$^{low}$HLA-DR+CD16+ monocytes were more potent inducers (FIG. 5C).

In order to investigate whether it is membrane TNF-α which mediates CD8+FOXP3+ Treg induction, CD8+ T cells and whole monocytes were isolated and analyzed a time course of their interactions by FACS. Within 10 min of culture with anti-CD3 mAb, an increase in the formation of CD8+ T cell and monocyte conjugates was observed, which decreased after 60 min of culture (FIG. 5D).

Next, Amnis ImageStream technology, which merges fluorescent microscopy with flow cytometry, was employed to examine the synapse between CD8+ T cells and monocytes. We observed an initial equal distribution of membrane TNF-α on the surface of unstimulated monocytes. After 10 min of culture with anti-CD3 mAb, membrane TNF-α clustered at the point of CD8+ T cell-monocyte interaction (FIG. 5E).

To further confirm the importance of CD8+ T cell and monocyte interactions for CD8+FOXP3+ Treg induction, PBMC from RA patients were cultured with anti-CD3 mAb for 20 minutes before isolating CD8+ T cells alone and CD8+ T cell-monocyte conjugates by sorting via flow cytometry. After a further 24 h of culture in media FOXP3 expression was observed only in the CD8+ T cells that had interacted with monocytes (FIG. 5F).

To exclude the possibility that anti-CD3 mAb was driving the induction of CD8+FOXP3+ Treg via activation of monocytes through Fc receptors, rather than a T cell specific effect, monocytes were isolated and fixed and then reintroduced to autologous PBMC depleted of monocytes and cultured with a F(Ab)$_2$ of Otelixizumab or OKT3. This successfully induced FOXP3 expression in CD8+ T cells (FIG. 5G). These results show that CD8+FOXP3+ Treg induction is not mediated by a soluble factor or via generic antibody activation of monocytes.

Example 5

Moderating Membrane TNF-α Expression by Monocytes Influences CD8+ T Cell Conversion into CD8+FOXP3+ Treg As described above, it has been observed that the expression of membrane TNF-α by monocytes is essential for the induction of CD8+FOXP3+ Treg by anti-CD3 mAb. To determine the importance of membrane TNF-α for the conversion of CD8+ T cells into CD8+FOXP3+ Treg and to determine whether those individuals whose CD8+ T cells did not induce FOXP3 expression could be converted to respond to anti-CD3 mAb, PBMC were pre-incubated with a TNF-α protease inhibitor (TAPI) for 1 h at room temperature. This prevented the cleavage of membrane TNF-α to soluble TNF-α resulting in the increased expression of membrane TNF-α by monocytes (FIG. 6A). After culture with anti-CD3 mAb, increased expression of membrane TNF-α on monocytes was observed; however, the maximal induction of CD8$^+$FOXP3$^+$ Treg from prior non-responders was approximately 50% under these conditions (FIG. 6B). Interestingly, this effect was not observed in healthy individuals after incubation with TAPI (FIG. 6C) even though healthy monocytes increased their expression of membrane TNF-α (data not shown).

Next, CD8$^+$ T cells from RA patients were cultured with autologous monocytes or allogeneic monocytes from RA patients with either high or low expression of membrane TNF-α in the presence of anti-CD3 mAb for 24 h. It was discovered that co-culture of responder CD8$^+$ T cells in the presence of anti-CD3 mAb with allogeneic monocytes expressing low levels of membrane TNF-α ablated CD8$^+$ FOXP3$^+$ Treg induction, whilst culture with allogeneic monocytes expressing high levels of membrane TNF-α restored CD8$^+$FOXP3$^+$ Treg induction (FIG. 6D). Interestingly, co-culture of non-responder CD8$^+$ T cells with allogeneic monocytes expressing high levels of membrane TNF-α rescued induction of FOXP3 expression in some individuals (FIG. 6D). However, in healthy individuals and a minority of RA patients (approximately 25%), CD8$^+$ T cells are unable to induce FOXP3 expression, despite the presence of low or high membrane TNF-α producing monocytes.

Example 6 p38 Phosphorylation Inhibits CD8+FOXP3+ Treg Induction

Based on the observation that a minority of CD8$^+$ T cells are unable to induce FOXP3 expression in the presence of membrane TNF-α producing monocytes, the signaling pathways that govern the induction of CD8$^+$FOXP3$^+$ Treg by anti-CD3 mAb were investigated. TCR, CD28 and TNFRII signaling, which have overlapping pathways, are required for the induction of CD8$^+$FOXP3$^+$ Treg. To dissect the differences between the three signals, responder and non-responder CD8$^+$ T cells were isolated and cultured with agonist antibodies against CD3, CD28 and TNFRII for 30 minutes. It was determined that this was the time period that CD8$^+$ T cells interact with monocytes in the presence of anti-CD3 mAb (FIG. 5D). A phosphorylation array was then used on lysates from the CD8$^+$ T cells. It was determined that responder CD8$^+$ T cells had reduced phosphorylation of p38 and Erk, but did not differ in their other phosphorylation targets from non-responder CD8$^+$ T cells (FIG. 7A).

Western blots were performed on isolated responder and non-responder CD8+ T cells exposed to the same conditions as the phosphorylation array, for the expression of phosphorylated p38 and Erk, to validate the array results. Interestingly, it was confirmed that responder CD8$^+$ T cells have reduced phosphorylation of p38 compared to non-responder CD8$^+$ T cells (FIG. 7B). However, no differences for the phosphorylation of Erk were observed (data not shown).

In order to determine if inhibiting p38 phosphorylation would rescue the induction of FOXP3 expression in CD8$^+$ T cells unresponsive to CD3-specific stimulation, a highly specific p38 MAPK inhibitor, BIRB 796, was used, which induces a conformational change in p38 and prevents it being phosphorylated. It was observed that pre-incubation of PBMC from patients with the p38 MAPK inhibitor resulted in FOXP3 expression by CD8$^+$ T cells that did not initially respond to CD3-specific stimulation (FIG. 7C). The p38 inhibitor did not alter the response of CD8$^+$ T cells that could already induce FOXP3 expression after culture with anti-CD3 mAbs.

Experimental Procedures

Study subjects. Patients with RA were recruited who fulfilled the revised classification criteria of the American College of Rheumatology for RA (FIG. 9). In addition, patients with PsA, OA or healthy volunteers were also recruited as controls for this study. All subjects signed informed consent. The University College London Hospital Ethics Committee approved the study.

Isolation of cell populations. PBMC were isolated by Ficoll-Paque Plus (GE Healthcare) gradient centrifugation, resuspended to $10^7$ cells/ml in FCS (Biosera) and 5% DMSO (Sigma-Aldrich), and frozen until subsequent use. CD8$^+$ T cells were negatively isolated and monocytes, CD4$^+$ T cells or B cells were depleted from PBMCs by positive selection with magnetic beads (Miltenyi, Biotec). Monocyte subsets or CD8$^+$ T cells interacting with monocytes were FACS sorted with the FACSAria (Beckton, Dickinson) based on expression of HLA-DR and CD14 or CD8 respectively.

Cell Cultures. For CD8$^+$FoxP3$^+$ Treg induction, PBMC were cultured with anti-CD3 mAb (OKT3 (e-bioscience), HIT3A (e-bioscience), UCHT1 (e-bioscience), Otelixizumab (GSK)) or anti-CD3 F(Ab)$_2$ (GSK) in RPMI1640, (Sigma-Aldrich), 10% fetal calf serum (Biosera) or human serum type AB (Lonza), 100 U/mg/ml penicillin/streptomycin (Sigma-Aldrich) for 24 h or 5 d. Alternatively, 1 µg/ml of agonist antibodies against CD28 (e-bioscience) or TNFRII (Hycult Biotech) in combination with OKT3 were utilized in PBMC cultures depleted of monocytes. For cytokine neutralization cultures, PBMC were cultured with OKT3 alone or in the presence of an isotype control or 10 µg/ml anti-TNF-α (R&D systems) or anti-IL-1β mAbs (R&D systems), 12.5 µg/ml anti-TGF-β mAb (R&D systems) or 0.1 µg/ml anti-IL-6 mAb (R&D systems). To inhibit monocyte activation of CD8$^+$ T cells, 10 µg/ml anti-CD80 (R&D systems) or anti-CD86 (R&D systems) were utilized. To convert a non-responder CD8$^+$ T cell into a responder, whole PBMC were incubated with 10 µg/ml TAPI (Enzo Life Sciences) for 1 h at room temperature, or with 5 µM selective p38 MAPK inhibitor, BIRB 796 (Merck Millipore), for 2 hours at 37° C. before culture with OKT3.

Suppression assay. After PBMC isolation, $2\times10^7$ cells were frozen whilst the remaining cells were plated out with 1 µg/ml OKT3. After 3 d, supernatants were removed and the cells were rested in media for 2 d. CD8$^+$ T cells were then isolated by negative selection and subsequently split into CD8$^+$CD25$^+$ or CD8$^+$CD25$^-$ T cells by positive selection with magnetic beads (purities for FOXP3>80%) (Miltenyi Biotec). Frozen cells were then thawed and their CD8$^+$ T cells were isolated. The PBMC depleted of CD8$^+$ T cells were stained with 1 µM CFSE then cultured at $1\times10^5$ cells with untouched CD8$^+$ T cells, CD8$^+$CD25$^+$ T cells or CD8$^+$CD25$^-$ T cells at various ratios. Cultures were then stimulated with 1 µg/ml staphylococcal antigen type B (SEB), cultured for 3 or 5 d and CD4$^+$ T cell proliferation was analyzed. Supernatants were stored for cytokine analysis.

Flow cytometry and soluble cytokine detection. Cell surface staining and intracellular staining were performed using the eBioscience FOXP3 staining buffer set as per manufacturers' instructions. For CD8$^+$ T cell staining, CD8-FITC and CD4-V450 were used to identify a pure CD8$^+$ T cell population. CD25-PECy7, TNFRII-APC, CTLA-4-PE, TGFβ-APC were used for characterization. For monocyte and B cells staining, CD14-APC, CD16-PE, HLA-DR-PECy7, CD19-APC were used in combination with membrane TNFα-PE. FOXP3-PE was used to detect intracellular FOXP3. For analysis of human intracellular cytokine production, PBMC were stimulated for 4 h with 50 ng/ml PMA, 250 ng/ml ionomycin (Sigma-Aldrich), and Golgi-Plug (BD, Biosciences) in complete medium. IFN-γ-PECy7, IL-10-APC, IL-2-APC, IL-17-APC, TNF-α-APC and appropriate isotype controls were utilized. For staining of membrane TNF-α versus soluble TNF-α production by monocytes, PBMC were cultured with anti-CD3 mAb alone, or after pre-incubation with TAPI, for 24 h. Supernatants were subsequently removed and replaced with the aforementioned stimulation mix for 4 h. PBMC were then stained for CD14-APC and membrane TNF-α-PE, before intracellular staining for TNF-α-FITC. Data were acquired on an LSRII (Beckton, Dickinson) and analyzed with FlowJo (TreeStar). IL-17 and IFN-γ levels from suppression assay supernatants were measured by mosaic ELISA (R&D Systems) as described by manufacturer's instruction and analyzed by Quansys Q-View™ Software (R&D Systems).

Amnis ImageStream. Monocytes were isolated by positive selection of CD14 (purities >95%) and stained with CD14-APC, CD8$^+$ T cells were purified by negative selection (purity >95%) and stained with CD8-FITC. Approximately 500 000 cells were co-cultured at a ratio of 1 CD8$^+$ T cell to 5 CD14$^+$ monocytes in the presence of anti-CD3 mAb for 0 and 10 min. Samples were fixed in 2% PFA for 10 min before being packaged and transported to Seattle to be processed by ImageStream. Data were processed with Ideas 4.0 software (Amnis).

Human Phospho-Kinase Array Kit. A human phospho-kinase array kit (R&D Systems) was used to detect phosphorylated kinases simultaneously. Capture antibodies are spotted in duplicate. Cell lysates (25 µg) from CD8$^+$ T cells that were negatively isolated (purity >95%) and cultured with 1 µg/ml of agonist antibodies against CD28, TNFRII and OKT3 for 30 min, were incubated with the membrane overnight in the buffer provided according to the manufacturer's protocol. Target proteins were captured with their respective antibodies. After washing, the membranes were incubated with Streptavidin-Horseradish Peroxidase to allow the chemiluminescent detection of captured kinases that are phosphorylated. Array data on X-ray film images were analyzed using image analysis software (ImageJ 1.46, NIH).

Western blot. CD8$^+$ T cells were isolated and cultured under the same conditions for analysis by the human phospho-kinase array kit. Cells were lysed using a lysis buffer (Invitrogen) supplemented with protease and phosphatase inhibitors. 25 µg of cell protein in lysate were separated by sodium dodecyl sulfate-polyacrylamide gel electrophoresis (SDS-PAGE) and then transferred onto nitrocellulose membranes (Millipore). Membranes were blocked in 5% non-fat milk/PBS, 0.5% Tween 20 (PBST) at room temperature for 1 h, and then incubated with anti-p-p38$_{Thr180/Tyr182}$ antibody (Cell Signaling Technology) before being washed in PBST and incubated with peroxidase-conjugated secondary antibody. After an additional wash, peroxidase activity was detected with the ECL system (GE Healthcare). Membranes were stripped and reprobed with anti-p38 antibody from (Cell Signaling Technologies), then developed, then stripped again and reprobed with anti-GAPDH antibody (Cell Signaling Technologies) to determine equivalency of loading. Exposed X-ray films were quantified by densitometric band analysis with ImageJ.

Statistical analysis. Values are expressed as absolute mean±SEM. Data were analyzed for significance in GraphPad Prism (La Jolla, Calif.) by two-tailed t test, paired t test, or one-way ANOVA as specified. Correlation coefficients and their significance were calculated by two-tailed Spearman's rank correlation.

All publications mentioned in the above specification are herein incorporated by reference. Various modifications and variations of the described methods and system of the invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the described modes for carrying out the invention which are obvious to those skilled in molecular or cell biology, autoimmunity or related fields are intended to be within the scope of the following claims.

The invention claimed is:

1. A method for inducing CD8$^+$FOXP3$^+$ regulatory T cells in a subject which comprises administering to the subject:
(i) a first agent which inhibits p38 phosphorylation; and
(ii) a second agent which is an anti-CD3 antibody;
wherein the subject is a non-responder to anti-CD3 therapy alone, showing no significant increase in FOXP3 expression on CD8$^+$ T cells following anti-CD3 stimulation, and wherein the first agent is administered to the subject followed by the second agent or the two agents are administered simultaneously.

2. A method according to claim 1, wherein the first agent is a p38 inhibitor selected from the group consisting of Tocriset, Pamapimod, AMG-548, SD282, SB239063, SB203580, SB220025, SKF86002, PD169316, PH-797804, SB202190, SC68376, VX702, VX745, R130823, AMG548, BIRB796, SCIO469, SCIO323, FR167653, MW12069ASRM, SD169, RWJ67657, and ARRY79.

3. A method according to claim 2, wherein the p38 inhibitor is BIRB 796.

4. A method according to claim 1, wherein the CD3 antibody is selected from the following: OKT3, HIT3A, UCHT1, Teplizumab and Otelixizumab.

5. A method for treating an autoimmune and/or inflammatory condition in a subject which comprises inducing CD8$^+$FOXP3$^+$ regulatory T cells in a subject by a method according to claim 1, wherein said autoimmune and/or inflammatory condition is selected from: pancreatitis, type I diabetes (IDDM), Graves Disease, inflammatory bowel disease (IBD), Crohn's Disease, ulcerative colitis, multiple sclerosis, rheumatoid arthritis, juvenile idiopathic arthritis, systemic lupus erythematosus, psoriasis, ankylosing spondylitis, scleroderma, systemic sclerosis, psoriatic arthritis, atopic dermatitis, vitiligo, Sjogren's syndrome, glomerulonephritis, IgA nephropathy, atopic dermatitis and anti-phospholipid syndrome.

6. A method according to claim 5, wherein the autoimmune and/or inflammatory condition is rheumatoid arthritis (RA).

7. A method according to claim 1, wherein the CD3 antibody is Otelixizumab.

8. A method of treating an autoimmune and/or inflammatory condition in a subject, comprising administering to the subject a first agent which inhibits p38 phosphorylation in CD8+ T cells and a second agent which is an anti-CD3 antibody, wherein the first agent enhances the efficacy of an anti-CD3 antibody, and wherein the subject is a non-responder to anti-CD3 therapy alone, showing no significant increase in FOXP3 expression on CD8$^+$ T cells following anti-CD3 stimulation, and wherein the first agent is administered to the subject followed by the second agent or the two agents are administered simultaneously, and wherein the autoimmune and/or inflammatory condition is selected from: pancreatitis, type I diabetes (IDDM), Graves Disease, inflammatory bowel disease (IBD), Crohn's Disease, ulcerative colitis, multiple sclerosis, rheumatoid arthritis, juvenile idiopathic arthritis, systemic lupus erythematosus, psoriasis, ankylosing spondylitis, scleroderma, systemic sclerosis, psoriatic arthritis, atopic dermatitis, vitiligo, Sjogren's syndrome, glomerulonephritis, IgA nephropathy, atopic dermatitis and anti-phospholipid syndrome.

9. The method according to claim 8, wherein the autoimmune and/or inflammatory condition is rheumatoid arthritis.

10. The method according to claim 8, wherein the agent which inhibits p38 phosphorylation in CD8+ T cells increases the proportion of patients that respond to the anti-CD3 antibody.

11. A method according to claim 8, wherein the autoimmune and/or inflammatory condition is rheumatoid arthritis (RA), and wherein the p38 inhibitor is BIRB 796.

* * * * *